(12) United States Patent
Netravali et al.

(10) Patent No.: US 10,179,807 B2
(45) Date of Patent: Jan. 15, 2019

(54) CROSSLINKED THERMOSET RESINS AND METHODS THEREOF

(71) Applicant: CORNELL UNIVERSITY, Ithaca, NY (US)

(72) Inventors: Anil N. Netravali, Ithaca, NY (US); Trina Ghosh Dastidar, Chandler, AZ (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/650,206

(22) PCT Filed: Dec. 9, 2013

(86) PCT No.: PCT/US2013/073956
§ 371 (c)(1),
(2) Date: Jun. 5, 2015

(87) PCT Pub. No.: WO2014/089578
PCT Pub. Date: Jun. 12, 2014

(65) Prior Publication Data
US 2015/0315249 A1 Nov. 5, 2015

Related U.S. Application Data

(60) Provisional application No. 61/734,842, filed on Dec. 7, 2012.

(51) Int. Cl.
*C07K 14/415* (2006.01)
*C08J 5/00* (2006.01)
(Continued)

(52) U.S. Cl.
CPC ............ *C07K 14/415* (2013.01); *C08H 1/00* (2013.01); *C08H 1/02* (2013.01); *C08H 99/00* (2013.01);
(Continued)

(58) Field of Classification Search
CPC ........... C07K 14/415; C08H 1/00; C08H 1/02
See application file for complete search history.

(56) References Cited

U.S. PATENT DOCUMENTS 2,137,973 A * 11/1938 Daly .................. C13K 1/06
127/38
2,930,700 A * 3/1960 Bradof ................. A23L 1/2118
426/312
(Continued)

FOREIGN PATENT DOCUMENTS

WO WO 2013079680 A1 * 6/2013 ............ C09J 177/12

OTHER PUBLICATIONS

Parovuori, Petteri, et al. "Oxidation of potato starch by hydrogen peroxide." Starch- Stärke 47.1 (1995): 19-23.*
(Continued)

*Primary Examiner* — Nicholas E Hill
(74) *Attorney, Agent, or Firm* — FisherBroyles, LLP; Andrew K. Gonsalves, Esq.

(57) ABSTRACT

The present invention relates to a method of making a crosslinked thermoset resin. One embodiment of this method comprises: (i) separating a plant-derived flour mixture into a protein fraction comprising proteins and a carbohydrate fraction comprising carbohydrates; (ii) subjecting the carbohydrate fraction to an oxidizing agent to yield oxidized carbohydrates comprising aldehyde functional groups or both aldehyde functional groups and carboxyl functional groups; and (iii) reacting the oxidized carbohydrates with the protein fraction under conditions effective to crosslink the proteins, thereby yielding a crosslinked thermoset resin. The present invention also relates to a crosslinked thermoset resin and composites, nanofiber membranes, and adhesives comprising the crosslinked thermoset resin.

20 Claims, 12 Drawing Sheets

(51) Int. Cl.
*C08H 1/00* (2006.01)
*C08H 1/02* (2006.01)
*C09J 189/00* (2006.01)
*C08L 89/00* (2006.01)
*C08H 99/00* (2010.01)
*C08J 5/18* (2006.01)
*C08J 3/24* (2006.01)
*C08J 5/04* (2006.01)
*C08J 5/24* (2006.01)
*C08K 7/02* (2006.01)
*C08L 1/04* (2006.01)

(52) U.S. Cl.
CPC .............. *C08J 3/246* (2013.01); *C08J 5/00* (2013.01); *C08J 5/04* (2013.01); *C08J 5/18* (2013.01); *C08J 5/24* (2013.01); *C08K 7/02* (2013.01); *C08L 1/04* (2013.01); *C08L 89/00* (2013.01); *C09J 189/00* (2013.01); *C08J 2303/04* (2013.01); *C08J 2329/04* (2013.01); *C08J 2389/00* (2013.01); *C08J 2489/00* (2013.01); *C08L 2205/16* (2013.01)

(56) References Cited

U.S. PATENT DOCUMENTS

| | | | |
|---|---|---|---|
| 5,371,194 A | 12/1994 | Ferretti | |
| 6,306,997 B1 | 10/2001 | Kuo et al. | |
| 6,518,387 B2 | 2/2003 | Kuo et al. | |
| 8,541,001 B2 | 9/2013 | Netravali et al. | |
| 2002/0137899 A1 | 9/2002 | Margolin et al. | |
| 2005/0274291 A1* | 12/2005 | Reddy ............... | C04B 28/06 106/692 |
| 2007/0148339 A1 | 6/2007 | Wescott et al. | |
| 2008/0004376 A1* | 1/2008 | Jong ............... | C08L 13/00 524/17 |
| 2011/0100256 A1* | 5/2011 | Anderson ............ | C09D 103/02 106/126.1 |
| 2012/0149813 A1* | 6/2012 | Kelly ............... | C08J 5/043 524/53 |
| 2014/0134497 A1* | 5/2014 | Lester ............... | D21H 23/48 429/249 |

OTHER PUBLICATIONS

Jong, Lei. "Rubber composites reinforced by soy spent flakes." Polymer international 54.11 (2005): 1572-1580.*
Jong, Lei. "Synergistic Reinforcement Effect of Soy Carbohydrate and Soy Protein in Polymer Composites." Proceedings of American Chemical Society National Meeting. vol. 93. 2005.*
Jong, Lei. "Effect of soy spent flakes and carbon black co-filler in rubber composites." Composites Part A: Applied Science and Manufacturing 38.2 (2007): 252-264.*
Yasir, S. Bin Md, et al. "The impact of Maillard cross-linking on soy proteins and tofu texture." Food chemistry 104.4 (2007): 1502-1508.*
International Search Report and Written Opinion issued in PCT/US2013/073956, dated Mar. 21, 2014.
Sujito, "Development of Green Resin Using Solid Waste Protein Soybean Curd "Tofu" Production," *Journal of Tropical Life Science*, 1(1):32-36(2010).
Allen et al., "Investigations of the Molecular Interactions of Soy-Based Adhesives," *Forest Products Journal*, 60(6):534-540 (2010).
Ghosh Dastidar et al., "'Green' crosslinking of native starches with malonic acid and their properties," *Carbohydrate Polymers*, 90:1620-1628 (2012).

* cited by examiner

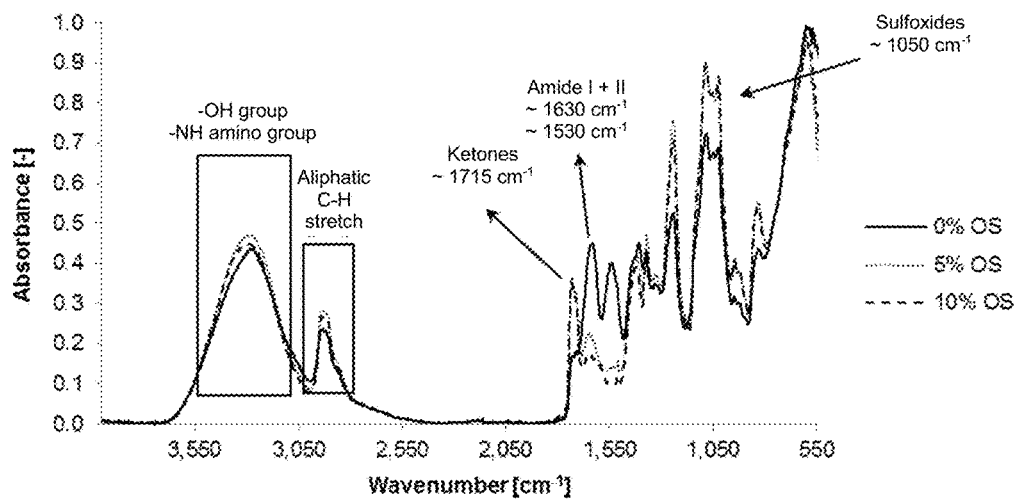
FIG. 16
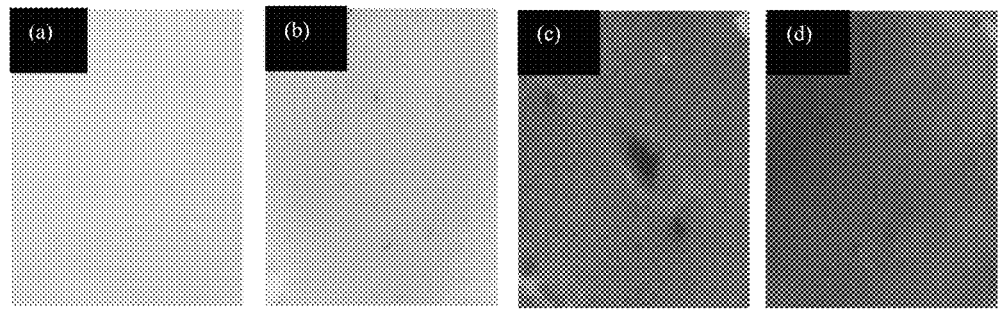
FIG. 17A   FIG. 17B   FIG. 17C   FIG. 17D
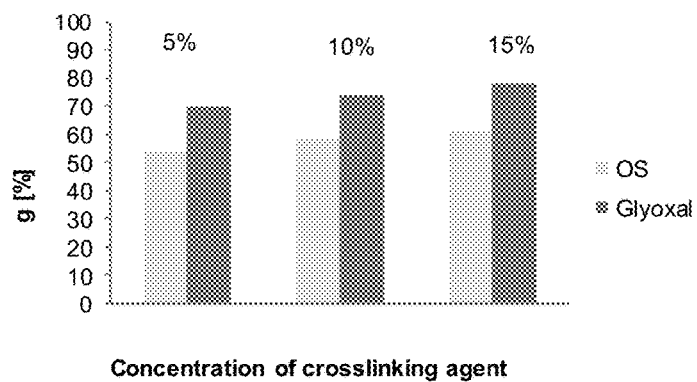
FIG. 18

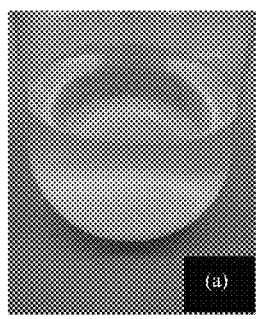 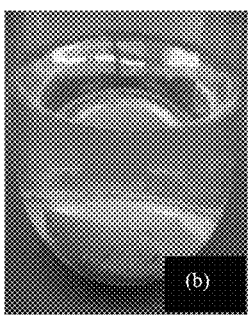 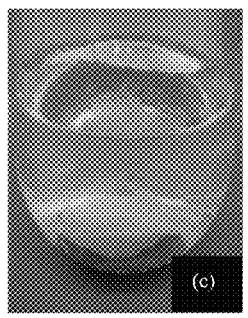 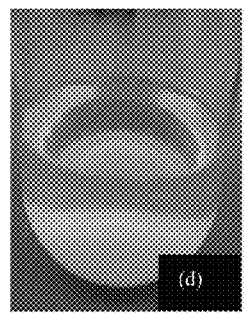
FIG. 19A    FIG. 19B    FIG. 19C    FIG. 19D
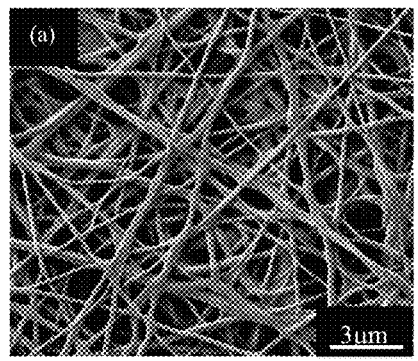 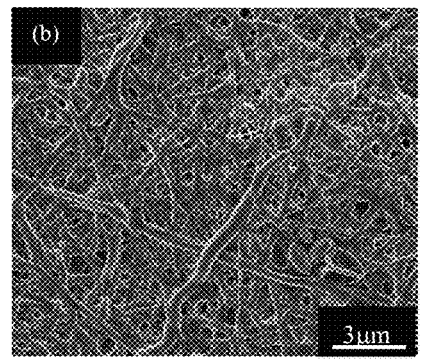
FIG. 20A    FIG. 20B ns and ME## CROSSLINKED THERMOSET RESINS AND METHODS THEREOF

CROSS-REFERENCE TO RELATED APPLICATIONS

This application is a U.S. National Phase filing under 35 U.S.C. § 371 of International Application No. PCT/US2013/073956, filed Dec. 9, 2013, and published as WO 2014/089578-A1 on Jun. 12, 2014, which claims benefit of priority from U.S. Provisional Patent Application Ser. No. 61/734,842, filed Dec. 7, 2012. The entire contents of each of the prior applications are incorporated herein by reference in their entirety.

FIELD OF THE INVENTION

The present invention relates to a crosslinked thermoset resin, methods of making a crosslinked thermoset resin, and composites, nanofiber membranes, and adhesives comprising a crosslinked thermoset resin.

BACKGROUND OF THE INVENTION

Polymers are used in diverse applications from disposable plastic bottles to housing and from aerospace and automobile parts to packaging. Most of these plastics are made using petroleum as raw material (R. Bhardwaj et al., Biomacromolecules, 2006, 7, 2044-2051; M. S. Huda et al., Journal of Materials Science, 2005, 40, 4221-4229; and W. J. Liu et al., Polymer, 2005, 46, 2710-2721). However, petroleum, a fossil resource, is finite and by some estimates we are consuming petroleum at 100,000 times the rate at which the earth can produce (E. S. Stevens, Biocycle, 2003, 44, 24-27; and E. S. Stevens, Biocycle, 2002, 43, 42-45). In addition, composites, where two dissimilar constituents are combined cannot be recycled or reused easily and about 95% of them end up in landfills at the end of their life. As a result, increased attention has been paid in the past decade to developing polymers and composites using renewable resources. Other factors contributing to this 'Sustainability Drive' are the abundant availability of the biomass at relatively low cost and significant environmental benefits including zero or low carbon footprint (A. N. Netravali and S. Chabba, Materials Today, 2003, 22-29; and N. Supanchaiyamat et al., Green Chemistry, 2012, 14).

Soy protein is commercially available as defatted soy flour (SF), soy protein concentrate (SPC) and soy protein isolate (SPI). Soy protein is a long chain molecule (polymer) consisting of 18 different polar and nonpolar amino acids. Polar amino acids such as cysteine, arginine, lysine, histidine and others can be used to crosslink the protein to improve mechanical, thermal and physical properties as well as reduce water sensitivity and hydrophilicity (S. Chabba and A. N. Netravali, Journal of Material Science, 2005, 40, 6263-6273; and J. T. Kim and A. N. Netravali, Journal of Agricultural and Food Chemistry, 2010, 58, 5400-5407). Such crosslinked soy protein can be used as 'green' biopolymer (resin) as replacement for currently used petroleum based polymers (A. Gonzalez et al., Journal of Food Engineering, 2011, 106, 331-338; X. Huang and A. N. Netravali, Biomacromolecules, 2006, 7, 2783-2789; S. K. Lingamoorthy, Master of Science, Cornell University, 2010; P. Lodha and A. N. Netravali, Polymer composites, 2005 26, 647-659; X. Huang and A. N. Netravali, Compos Sci Technol, 2009, 69, 1009-1015; X. Huang and A. N. Netravali, Composites Science and Technology, 2009, 69, 1009-1025; X. Huang and A. N. Netravali, Journal of Macromolecular Science, Part A: Pure and Applied Chemistry, 2008, 45, 899-906; X. S. Huang and A. Netravali, Compos Sci Technol, 2007, 67, 2005-2014; and R. Nakamura, A. N. Netravali, et al., Fire and Materials, 2013, 37, 75-90). Another advantage of the soy protein based resin, besides being green, is that it is inherently fire resistant and can perform better than some petroleum based resins (R. Nakamura, A. N. Netravali, et al., Fire and Materials, 2013, 37, 75-90).

It has been reported that soy proteins can be crosslinked using aldehydes such as formaldehyde, glutaraldehyde (GA), glyoxal and glyceraldehyde through Maillard reactions (S. B. M. Yasir et al., Food Chemistry, 2007, 104, 1502-1508). Park et al. (Journal of the American Oil Chemists' Society, 2000, 77) crosslinked SPI with GA to produce biopolymers with enhanced mechanical properties. Chabba et al. (Green Chemistry, 2005, 7, 576-581) crosslinked SF with GA which also led to an increase in Young's modulus with crosslinking Huang and Netravali (Compos Sci Technol, 2009, 69, 1009-1015) have reported the use of (3-isocyanatopropyl) triethoxysilane (ITES) for crosslinking of SPC. However, in moving towards 'sustainable' products, clean syntheses, use of natural renewable reagents and water based processing become highly desirable.

Nanofiber based membranes have been used in myriad of applications (G. Kim et al., J. Biomed. Mater. Res. Part. B Appl. Biomater., 2007, 81, 104-110; J. S. Im et al., Carbon, 2010, 48, 2573-2581; J. Y. Lee et al., Biomaterials, 2009, 30, 4325-4335; M. Alcoutlabi et al., J. Mater. Sci., 2013, 48, 2690-2700; W. Zhang et al., Appl. Phys. Lett., 2009, 95, 043304/1-043304/3; J. Fang et al., J., Chin. Sci. Bull., 2008, 53, 2265-2286; and D. F. Emerich et al., Curr. Nanosci., 2005, 1, 177-188). Almost all currently used membranes are made using non-biodegradable polymers derived from petroleum (S. Y Gu et al., Synth. Met., 2005, 155, 157-161; Z. Ma et al., Biomaterials, 2005, 26, 2527-36; L. Ji et al., Nanotechnology, 2009, 20, 1-7; A. L. Martinez-Hernandez et al., Curr. Nanosci., 2010, 6, 12-39; D. G. Yu et al., Nanotechnology, 2009, 20, 055104/1-055104/9; H. Wu et al., NanoLetters, 2010, 10, 4242-4248; and H. Niu et al., Carbon, 2011, 49, 2380-2388). For such non-biodegradable materials, there are no environmentally acceptable end-of-life solutions as of now. Most of them, unfortunately, end up in landfills. Availability of environment-friendly, biodegradable and fully sustainable plant derived polymers such as proteins, starches and cellulose have slowly begun to change this scenario. Plant derived proteins and starches also tend to be inexpensive compared to petroleum based polymers. Other factors contributing to the current 'Green Movement' are the abundant availability of the biomass and the possibilities of water based 'green' processing. These advantages have also resulted in developing 'green' nanofiber based membranes as replacement for petroleum derived non-degradable ones that are currently being used (S. J. Lee et al., J. Biomed. Mater. Res. A, 2007, 83, 999-1008; S. Agarwal et al., Polymers, 2008, 49, 5603-5621; B. Y. Gui et al., J. Biomed. Mater. Res. A, 2010, 93, 158-163; S. A. Sell et al., Polymers, 2010, 2, 522-553; L. Malinova et al., Funct. Mater. Lett., 2011, 4, 365-368; and J. Schiffman et al., Polym. Rev., 2008, 48, 317-352). Unlike petroleum based materials, most plant based materials can be easily composted after their intended life without harming the nature.

There is great interest in developing green nanofiber membranes. Several papers describe production of nanofiber membranes prepared by electrospinning of soy protein blends with polyvinyl alcohol (PVA), polylactid acid (PLA), zein or polyethylene oxide (PEO) (C. Yao et al., J. Appl.

Polym. Sci., 2007, 30, 380-385; M. Phiriyawirut et al., *Adv. Mater. Res.*, 2008, 55-57, 733-736; A. C. Vega-Lugo et al., *Food Res. Int.*, 2009, 42, 933-940; and D. Cho et al., *Polymer Degradation and Stability*, 2012, 97, 747-754). However, disintegration of the nanofiber membranes in water is one of their biggest disadvantages.

This limitation can, however, be overcome by crosslinking of the polymer. Crosslinking has been the most commonly used technique to improve resistance to water as well as to improve the physical properties of polymers. Crosslinking is the process of chemically joining two or more molecules by a covalent bond. Crosslinking agents (or crosslinkers) are molecules that contain two or more reactive groups capable of chemically reacting with specific functional groups on proteins or other molecules. Despite the complexity of protein structure that contains several different amino acids, only a small number of protein functional groups comprise selectable targets for practical bioconjugation method (S. S. Wong et al., *National Institutes of Health*; CRC Press, USA, 1991). In fact, just four protein functional-group targets account for most of the crosslinking modifications. These include: (a) primary amines (—$NH_2$): this group exists at the N-terminus of each polypeptide chain and in the side chain of lysine and arginine residues; (b) carboxyls (—COOH): this group exists at the C-terminus of each polypeptide chain and in the side chains of aspartic acid and glutamic acid; (c) hydroxyl (—OH); and (d) sulfhydryls (—SH): this group exists in the side chain of cysteine. For each of these protein functional groups there exist one to several types of reactive groups that are capable of reacting with them and have been used as the basis for synthesizing crosslinking reagents (S. S. Wong et al., *National Institutes of Health*; CRC Press, USA, 1991). Most commonly used crosslinkers for amine groups are bi-functional compounds, such as glutaraldehyde and glyoxal. Several papers have described crosslinking reactions in protein based resins with glutaraldehyde or glyoxal (S. K. Park et al., *JAOCS*, 2000, 77, 879-884; and S. Chabba et al., *J. Mater. Sci.*, 2005, 40, 6275-6282). Both of these crosslinkers, however, are toxic and inappropriate from the environmentally-friendly point of view, and hence green crosslinkers are preferred.

The present invention is directed to overcoming these and other deficiencies in the art.

SUMMARY OF THE INVENTION

The present invention relates to a crosslinked thermoset resin, methods of making a crosslinked thermoset resin, and composites, nanofiber membranes, and adhesives comprising a crosslinked thermoset resin.

In one aspect, the present invention relates to a method of making a crosslinked thermoset resin. This method involves (i) separating a plant-derived flour mixture into a protein fraction comprising proteins and a carbohydrate fraction comprising carbohydrates; (ii) subjecting the carbohydrate fraction to an oxidizing agent to yield oxidized carbohydrates comprising aldehyde functional groups or both aldehyde functional groups and carboxyl functional groups; and (iii) reacting the oxidized carbohydrates with the protein fraction under conditions effective to crosslink the proteins, thereby yielding a crosslinked thermoset resin. In another aspect, the present invention relates to a crosslinked thermoset resin produced according to this method. In another aspect, the present invention relates to a composite comprising: (i) a crosslinked thermoset resin produced according to this method; and (ii) a natural fiber, a synthetic fiber, or a particulate plant material. In another aspect, the present invention relates to a nanofiber membrane comprising: (i) a crosslinked thermoset resin produced according to this method; and (ii) a nanofibrillated natural fiber, a nanofibrillated synthetic fiber material, or natural whiskers. In another aspect, the present invention relates to an adhesive comprising a crosslinked thermoset resin produced according to this method.

In another aspect, the present invention relates to a crosslinked thermoset resin comprising crosslinked proteins isolated from a plant source and crosslinked with an oxidized carbohydrate crosslinking agent intrinsic to the same plant source. In another aspect, the present invention relates to a composite comprising: (i) this crosslinked thermoset resin according; and (ii) a natural fiber, a synthetic fiber, or a particulate plant material. In another aspect, the present invention relates to a nanofiber membrane comprising: (i) this crosslinked thermoset resin according; and (ii) a nanofibrillated natural fiber, a nanofibrillated synthetic fiber material, or natural whiskers. In another aspect, the present invention relates to an adhesive comprising this crosslinked thermoset resin.

In another aspect, the present invention relates to a method of making a protein-based crosslinked thermoset resin. This method involves: (i) providing a denatured protein having exposed reactive functional groups; (ii) oxidizing a sugar with acidified hydrogen peroxide ($H_2O_2$) to yield an oxidized sugar having aldehyde functional groups or both aldehyde functional groups and carboxyl functional groups; and (iii) reacting the oxidized sugar with the denatured protein to yield a protein-based crosslinked thermoset resin. In another aspect, the present invention relates to a crosslinked thermoset resin produced according to this method. In another aspect, the present invention relates to a composite comprising: (i) a crosslinked thermoset resin produced according to this method; and (ii) a natural fiber, a synthetic fiber, or a particulate plant material. In another aspect, the present invention relates to a nanofiber membrane comprising: (i) a crosslinked thermoset resin produced according to this method; and (ii) a nanofibrillated natural fiber, a nanofibrillated synthetic fiber material, or natural whiskers. In another aspect, the present invention relates to an adhesive comprising a crosslinked thermoset resin produced according to this method.

In another aspect, the present invention relates to a method of making a crosslinked thermoset resin. This method involves: (i) providing a plant-derived flour mixture comprising a protein fraction comprising proteins and a carbohydrate fraction comprising carbohydrates; (ii) subjecting the plant-derived flour mixture to an oxidizing agent to yield an oxidized plant-derived flour mixture having oxidized carbohydrates comprising aldehyde functional groups or both aldehyde functional groups and carboxyl functional groups; and (iii) heating the oxidized plant-derived flour mixture under conditions effective to crosslink the proteins, thereby yielding a crosslinked thermoset resin. In another aspect, the present invention relates to a crosslinked thermoset resin produced according to this method. In another aspect, the present invention relates to a composite comprising: (i) a crosslinked thermoset resin produced according to this method; and (ii) a natural fiber, a synthetic fiber, or a particulate plant material. In another aspect, the present invention relates to a nanofiber membrane comprising: (i) a crosslinked thermoset resin produced according to this method; and (ii) a nanofibrillated natural fiber, a nanofibrillated synthetic fiber material, or natural whiskers. In another aspect, the present invention relates to an adhesive comprising a crosslinked thermoset resin produced according to this method.

In various aspects, the present invention provides sustainable products that involve clean syntheses and the use of natural renewable reagents and water based processing. In particular embodiments, the present invention provides methods where plant flour is crosslinked using a process that does not require an external crosslinking agent. Instead, the present invention provides a method that uses oxidized carbohydrates taken from the plant source as the crosslinking agent for the proteins. Although the present invention is not limited to using carbohydrates and proteins taken from the same source, in certain embodiments the present invention provides for the same plant being the source of both the oxidized carbohydrates (as the crosslinking agent) and the proteins to be crosslinked.

In an illustrative embodiment, the present disclosure provides a novel reaction scheme for crosslinking of defatted soy flour (SF) (see, e.g., FIG. 1), an inexpensive biobased material, without the use of any external crosslinker. Thus, no external chemicals are needed to obtain crosslinked (thermoset) soy protein resin. Besides obtaining better mechanical properties, crosslinking, to some extent, was also advantageous in reducing the moisture sensitivity of the soy protein resin. This technology can be easily extended to flours from other grains where the two components are protein and soluble carbohydrates in the form of sugars and/or low molecular weight starches.

This SF based crosslinked resin may be used with natural fibers to form green composites for many applications. The SF based resin may also be used with synthetic fibers such as aramid, graphite and many others to obtain composites with higher mechanical, physical and thermal properties. The resin may also be used as a 'green' adhesive.

The present invention also provides for the fabrication of soy protein and wheat gluten based nanofiber membranes. The present disclosure illustrates nanofiber crosslinking being carried out using a plant-based (also referred to herein as plant-derived) crosslinker. Crosslinking can improve the material properties, decrease moisture sensitivity and increase the useful life.

The present invention also provides fabrication of novel and inexpensive plant protein based nanofiber membranes prepared by electrospinning process. In an illustrative example, SF was successfully purified using an acid-wash process to increase the protein content and used as the major constituent material along with gluten for electrospinning process and successfully spun into nanofiber membrane with no polymer beads or other defects. PVA was used as 'helper material' for easy electrospinning. The higher stability of nanofiber membrane in water was achieved by crosslinking reaction without the use of any toxic crosslinking reagent. Oxidized sugars (OS), prepared by a benign $H_2O_2$ oxidizing process, was confirmed as a green crosslinking agent for protein based nanofiber membranes and films by FTIR and sol-gel test. The stability of protein based nanofiber membranes in water was confirmed by water soaking treatment. However, if kept away from water, such nanofiber structures can last for a long time.

The use of such nanofiber based membranes for filtering fine dust, bacteria or viruses filter is very promising (D. Lubasova et al., *J. Nanosci. Nanotech.*, 2013—In press). These protein based nanofiber membranes may also be used with other natural resins to develop composite materials with higher value-added products. Finally, some biotechnology applications also seem to be very interesting and possible. To outline future prospects; materials based on this protein based nanofiber membranes could be promising for tissue engineering, wound healing, or biosensors as well.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 16: ATR-FTIR spectra of the gluten/PSF/PVA nanofiber membranes before and after crosslinking with 5 and 10% of OS.

FIGS. 17A-17D: Films obtained from gluten/PSF/PVA [30/25/45] with OS: 0 (FIG. 17A), 5 (FIG. 17B), 10 (FIG. 17C), and 15% (FIG. 17D) after crosslinking.

FIG. 18: Gel (g) % obtained by the sol-gel analysis of gluten/PSF/PVA films crosslinked by glyoxal and OS.

FIGS. 19A-19D: Crosslinked films gluten/PSF/PVA immersed into DI water after 1 month with OS: 5 wt % (FIG. 19A), 10 wt % (FIG. 19B), 15 wt % (FIG. 19C), and without (FIG. 19D) crosslinking agent.

FIGS. 20A and 20B: Crosslinked nanofiber membranes gluten/PSF/PVA with 15% of OS after: 6 hrs water treatment (FIG. 20A) and 1 day water treatment (FIG. 20B) at room temperature.

DETAILED DESCRIPTION OF THE INVENTION

Figure 1:
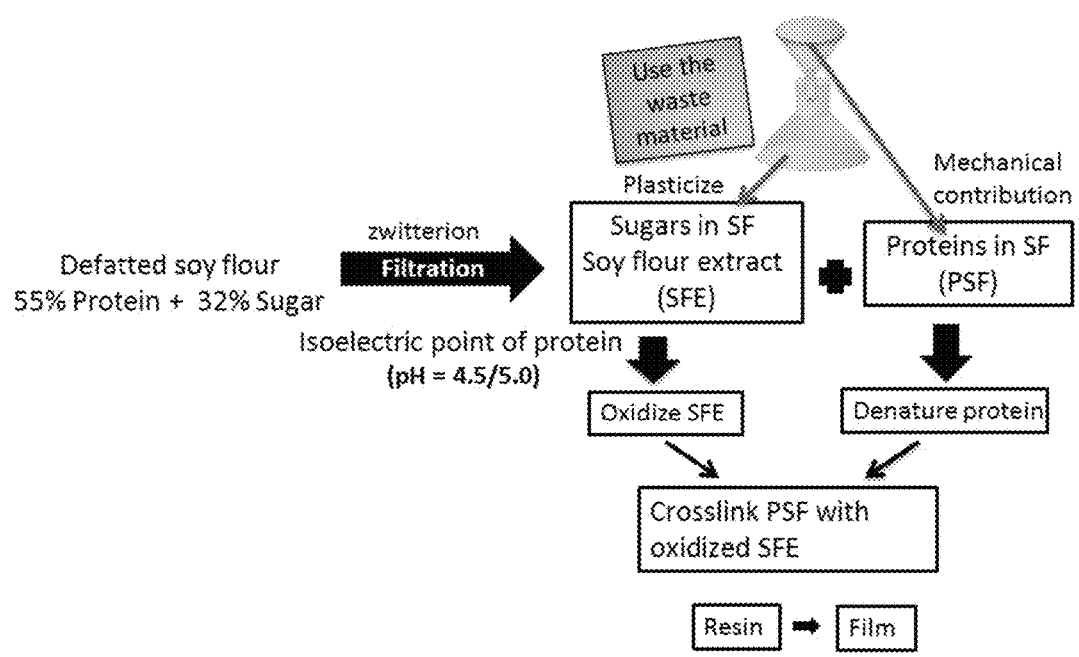
FIG. 1: Scheme showing crosslinking of SF using a novel three step process.

The present invention generally relates to a crosslinked thermoset resin, methods of making a crosslinked thermoset resin, and composites, nanofiber membranes, and adhesives comprising a crosslinked thermoset resin. In particular embodiments, the crosslinked thermoset resin is derived from a plant, and more particularly derived from a plant flour.

The plant or plant flour can be derived from any plant. However, for illustrative purposes, the present disclosure provides an illustrative embodiment of the use of soybean as the plant source for the crosslinked thermoset resin and the method of making the crosslinked thermoset resin.

For example, as an illustrative embodiment, the present disclosure provides a novel reaction scheme for crosslinking of defatted soy flour (SF), an inexpensive biobased material, without the use of any external crosslinker. In this illustrative embodiment, the method involves a three-step process that includes separating sugars in SF from protein, oxidizing the sugars to aldehydes and carboxylic acids and then reacting them with the protein. The resulting crosslinked SF resin shows enhanced thermal and mechanical properties and higher stability (resistance) in water. The present disclosure also provides that similar reactions can also be utilized to crosslink other proteins obtained from plants and animal sources with commercially available sugars oxidized using acidified hydrogen peroxide ($H_2O_2$). The method of the present disclosure provides a green, easy, and low cost method to crosslink proteins and, therefore, can be useful in making inexpensive biobased polymers and resins with enhanced mechanical properties. As provided herein, the method of the present disclosure also provides for the use of flours from other grains where the two components are protein and carbohydrates in the form of sugars and/or low molecular weight starches.

In one aspect, the present invention relates to a crosslinked thermoset resin comprising crosslinked proteins, where the proteins are isolated from a plant source and crosslinked with an oxidized carbohydrate crosslinking agent intrinsic to the same plant source.

As used herein, the term "intrinsic" is meant to describe the relationship that the carbohydrate crosslinking agent has to the proteins that are crosslinked. In particular, in accordance with the present disclosure, to be "intrinsic to the same plant source," the oxidized carbohydrate crosslinking agent is required to come from the same type of plant as the proteins to be crosslinked. However, the concept of being "intrinsic" does not require that the carbohydrate crosslinking agent is taken from the exact same single plant as the proteins being crosslinked. In other words, the carbohydrate crosslinking agent can come from plant "A" and the proteins can come from either plant "A" or plant "B" or any other plant, as long as the plants are at least of the same taxonomic family, or more particularly of the same taxonomic genus, or even more particularly of the same taxonomic species. Therefore, in a specific embodiment, both the carbohydrate crosslinking agent and the proteins to be crosslinked are taken from the same exact plant.

The plant source can be any plant or plant part that comprises both carbohydrates and proteins. Suitable plant parts can include any part of a plant that contains carbohydrates and/or proteins. Examples of suitable plant parts can include, without limitation, a bean, a seed, a seed kernel, a root, a shoot, a stem, a fruit, a tuber, and mixtures thereof. In a particular embodiment, the plant source can be a plant such as, but not limited to, a legume plant, a bean plant, and/or a grain plant. In other particular embodiments, the plant source is a plant such as, but not limited to, soybean, jatropha (e.g., *Jatropha curcus*), neem (e.g., *Azadiractha indica*), pea, peanut, karanja (e.g., *Pongamia pinnata*), wheat, maize, rice, and any other plant belonging to the same taxonomic families of any of the plants listed above.

The crosslinked thermoset resin of the present disclosure has improved mechanical properties, improved thermal properties, and/or reduced moisture absorption compared to a non-crosslinked resin from the same plant source. In certain embodiments, the crosslinked thermoset resin can have improved mechanical properties such as improved tensile strength (fracture stress), improved Young's modulus, or both. In certain other embodiments, the crosslinked thermoset resin can have improved thermal properties such as improved thermal degradation temperature.

The crosslinked thermoset resin can also be more stable in water than a non-crosslinked resin from the same source.

In another aspect, the present invention relates to a composite comprising: (i) this crosslinked thermoset resin according to the present disclosure; and (ii) a natural fiber, a synthetic fiber, or a particulate plant material. Methods of making such composites are known in the art.

In another aspect, the present invention relates to a nanofiber membrane comprising: (i) this crosslinked thermoset resin according; and (ii) a nanofibrillated natural fiber, a nanofibrillated synthetic fiber material, or natural whiskers. Methods of making such nanofiber membranes are known in the art.

In another aspect, the present invention relates to an adhesive comprising this crosslinked thermoset resin. Methods of making such adhesives are known in the art.

In one aspect, the present invention relates to a method of making a crosslinked thermoset resin. More particularly, the present invention relates to a method of making a crosslinked thermoset resin derived from a plant. In one embodiment, this method involves separating a plant-derived flour mixture into a protein fraction and a carbohydrate fraction, where the protein fraction comprises proteins and the carbohydrate fraction comprises carbohydrates. Thereafter, the method involves subjecting the carbohydrate fraction to an oxidizing agent to yield oxidized carbohydrates comprising aldehyde functional groups or both aldehyde functional groups and carboxyl functional groups. The method then involves reacting the oxidized carbohydrates with the protein fraction under conditions effective to crosslink the proteins, thereby yielding a crosslinked thermoset resin.

In one embodiment of this method, the step of separating the plant-derived flour mixture into the protein fraction and the carbohydrate fraction comprises performing either a water-based separation procedure or a solvent-based separation procedure. In various embodiments, the determination of whether to use a water-based separation procedure or a solvent-based separation procedure depends on whether the subject carbohydrates and proteins in the plant-derived flour mixture can be separated by water or whether solvents are needed. Those of ordinary skill in the art can readily determine which sort of separation process is suitable in the different plant-derived flour mixtures covered by the present disclosure.

In a particular embodiment, the water-based separation procedure comprises an isoelectric filtration process whereby the proteins are rendered insoluble at their isoelectric point in water while the carbohydrates remain soluble in water. As is well known by those of ordinary skill in the art, under isoelectric filtration processes, the pH of a solution containing carbohydrates and proteins can be adjusted to reach the isoelectric point of the proteins, thereby causing the proteins to become insoluble in water. The soluble carbohydrates and insoluble proteins can then be separated from one another through processes such as filtration. Therefore, using such a water-based separation procedure makes it unnecessary to use solvents (e.g., organic solvents) to separate the carbohydrates from the proteins.

For illustrative purposes, soybean flour can be used to illustrate one non-limiting example of the use of a water-based separation procedure to separate the proteins from the carbohydrates/proteins mixture derived from a soybean plant source. For example, if a solution containing carbohydrates and proteins from soy flour has a pH of 7.0, it can be adjusted to a pH of 4.5, which is the isoelectric point of the soy proteins, thereby rendering the soy proteins insoluble in water. In order to lower the pH of the solution, an acid such as hydrochloric acid (HCl) can be added to the solution until the pH is at the isoelectric point of the proteins. These same procedures can be used for any solution containing soluble carbohydrates and proteins from any plant source, as long as the isoelectric point of the proteins is known.

In one embodiment of this method, the step of reacting the oxidized carbohydrates with the protein fraction comprises: (i) denaturing the proteins of the protein fraction to expose reactive functional groups on the denatured proteins; and (ii) contacting the oxidized carbohydrates with the functional groups of the denatured proteins to crosslink the proteins.

As used herein, an "oxidizing agent" refers to a composition, compound, or any other agent that is effective to oxidize carbohydrates. In various embodiments, suitable oxidizing agents that are effective to oxidize carbohydrates are those compositions, compounds, or agents that react to carbohydrates and/or functional groups of the carbohydrates to yield oxidized carbohydrates comprising aldehyde functional groups or both aldehyde functional groups and carboxyl functional groups. Suitable oxidizing agents that are effective to oxidize carbohydrates are well known by those of ordinary skill in the art. Examples of suitable oxidizing agents for use in the present invention include, without limitation, $CrO_3$, $KMnO_4$, $HNO_3$, $HIO_6$, and any other composition effective to oxidize the carbohydrates.

In one embodiment, the oxidizing agent is a benign or non-toxic oxidizing agent that is effective to oxidize carbohydrates. Suitable benign or non-toxic oxidizing agents are well known by those of ordinary skill in the art. In a particular embodiment, the benign or non-toxic oxidizing agent is hydrogen peroxide ($H_2O_2$). In another embodiment, the benign or non-toxic oxidizing agent is acidified the hydrogen peroxide ($H_2O_2$).

As described herein, the oxidizing agent is effective to yield oxidized carbohydrates comprising aldehyde functional groups or both aldehyde functional groups and carboxyl functional groups. In certain embodiments, the aldehyde functional groups will be preferred. While carboxyl functional groups can commonly occur as a result of oxidation by the oxidizing agent, the oxidization process can be tuned in order to obtain maximum aldehyde functional groups and minimum carboxyl functional groups, depending on the desired aldehyde-to-carboxyl function group ratio. The same tuning process can be adopted in order to maximize the carboxyl functional groups relative to the aldehyde functional groups due to oxidation. Such tuning processes are known to those of ordinary skill in the art.

As described above, the method of making a crosslinked thermoset resin involves separating a plant-derived flour mixture into a protein fraction and a carbohydrate fraction, where the protein fraction comprises proteins and the carbohydrate fraction comprises carbohydrates. The carbohydrates of the carbohydrate fraction can comprise soluble carbohydrates and/or low molecular weight starches.

Soluble carbohydrates are well known to those of ordinary skill in the art. Examples of soluble carbohydrates include sugars, and more particularly soluble sugars. Suitable soluble sugars for use in the present invention include, without limitation, glucose, fructose, sucrose, raffinose, maltose, galactose, stachyose, and mixtures thereof. As provided herein, in particular embodiments, any soluble carbohydrate that can be subjected to oxidation to yield oxidized soluble carbohydrates can be used as the crosslinking agent in accordance with the methods described herein.

Low molecular weight starches are well known to those of ordinary skill in the art. Examples of low molecular weight starches include soluble starches or mixtures of soluble starches. As provided herein, in particular embodiments, any low molecular weight starch that can be subjected to oxidation to yield oxidized low molecular weight starches can be used as the crosslinking agent in accordance with the methods described herein.

As described above, the method of making a crosslinked thermoset resin involves the use of a plant-derived flour mixture, which mixture includes a protein fraction and a carbohydrate fraction. Suitable plant-derived flour mixtures can be from any plant or plant part that comprises both carbohydrates and proteins. Suitable plant parts can include any part of a plant that contains carbohydrates and/or proteins. Examples of suitable plant parts can include, without limitation, a bean, a seed, a seed kernel, a root, a shoot, a stem, a fruit, a tuber, and mixtures thereof. In a particular embodiment, the plant-derived flour mixture can be from a plant such as, but not limited to, a legume plant, a bean plant, and/or a grain plant. In other particular embodiments, the plant-derived flour mixture is from a plant such as, but not limited to, soybean, jatropha (e.g., *Jatropha curcus*), neem (e.g., *Azadiractha indica*), pea, peanut, karanja (e.g., *Pongamia pinnata*), wheat, maize, rice, and any other plant belonging to the same taxonomic families of any of the plants listed above.

Provided below is one illustrative example of an embodiment of the method of making a crosslinked thermoset resin that involves the use of a plant-derived flour mixture. In this embodiment, soy flour (SF) is crosslinked using the three-step process as shown in the scheme of FIG. 1. For example, in the first step, the protein from SF was separated from the water soluble carbohydrates consisting of small sugars using a simple lab scale filtration technique. The sugar extract obtained in water, is termed soy flour extract (SFE) while the separated protein is termed as purified soy flour (PSF). The PSF, confirmed to have over 65% protein, is close to that present in SPC. The SFE is generally found to be unusable (J. T. Kim and A. N. Netravali, *Journal of Agricultural and Food Chemistry*, 2010, 58, 5400-5407) since it is a mixture of 5 sugars; glucose, fructose, sucrose, raffinose and stachyose (K. Qiu and A. N. Netravali, *Composites Science & Technology*, In Press, 2012). In the second step of the process these sugars are converted to aldehydes and carboxylic acids by oxidation using hydrogen peroxide ($H_2O_2$), a green oxidizing agent. In the third step, the oxidized sugars, in SFE, are used as crosslinking agents to crosslink the PSF, utilizing the Maillard reaction. Thus, no external chemicals are needed to obtain crosslinked (thermoset) soy protein resin. Besides obtaining better mechanical properties, crosslinking, to some extent, is also advantageous in reducing the moisture sensitivity of the soy protein resin. Reactions to obtain aldehyde and carboxyl groups in SFE can be confirmed separately using commercially available glucose and sucrose and their crosslinking reactions can be further confirmed with SPI (90% protein). This technology can be easily extended to flours from other grains where the two components are protein and soluble carbohydrates in the form of sugars and/or low molecular weight starches. In various aspects, the present invention provides sustainable products that involve clean syntheses and the use of natural renewable reagents and water based processing.

In another aspect, the present invention relates to method of making a protein-based crosslinked thermoset resin. This method involves: (i) providing a denatured protein having exposed reactive functional groups; (ii) oxidizing a sugar with acidified hydrogen peroxide ($H_2O_2$) to yield an oxidized sugar having aldehyde functional groups or both aldehyde functional groups and carboxyl functional groups; and (iii) reacting the oxidized sugar with the denatured protein to yield a protein-based crosslinked thermoset resin.

In accordance with this method, suitable proteins for use in this method can include proteins from an animal source or a plant source.

As set forth herein, this particular method of making a protein-based crosslinked thermoset resin involves providing a denatured protein having exposed reactive functional groups. Methods for denaturing proteins to expose reactive functional groups are known in the art. The denaturation of the proteins depends on the proteins and the source of the proteins (e.g., the type of animal or plant source).

As set forth herein, this particular method of making a protein-based crosslinked thermoset resin also involves oxidizing a sugar with acidified hydrogen peroxide ($H_2O_2$) to yield an oxidized sugar having aldehyde functional groups or both aldehyde functional groups and carboxyl functional groups. Methods for oxidizing a sugar with acidified hydrogen peroxide ($H_2O_2$) to yield an oxidized sugar having aldehyde functional groups or both aldehyde functional groups and carboxyl functional groups are known in the art. Any sugars that can be oxidized with acidified $H_2O_2$ can be used in this method.

As set forth herein, this particular method of making a protein-based crosslinked thermoset resin further involves reacting the oxidized sugar with the denatured protein to yield a protein-based crosslinked thermoset resin. Methods of reacting an oxidized sugar with a denatured protein to yield a protein-based crosslinked thermoset resin are known in the art.

In another aspect, the present invention relates to a method of making a crosslinked thermoset resin from a plant-derived flour mixture that does not require the separation of the carbohydrates from the proteins from the flour mixture. This method involves: (i) providing a plant-derived flour mixture comprising a protein fraction comprising proteins and a carbohydrate fraction comprising carbohydrates; (ii) subjecting the plant-derived flour mixture to an oxidizing agent to yield an oxidized plant-derived flour mixture having oxidized carbohydrates comprising aldehyde functional groups or both aldehyde functional groups and carboxyl functional groups; and (iii) heating the oxidized plant-derived flour mixture under conditions effective to crosslink the proteins, thereby yielding a crosslinked thermoset resin. In another aspect, the present invention relates to a crosslinked thermoset resin produced according to this method.

In accordance with this method, suitable plant-derived flour mixtures can include any of those as described herein.

In accordance with this method, suitable oxidizing agents can include any of those as described herein.

In accordance with this method, the step of heating the oxidized plant-derived flour mixture involves heating the oxidized plant-derived flour mixture to a suitable temperature and for a suitable time to crosslink the proteins contained in the oxidized plant-derived flour mixture.

In another aspect, the present invention relates to a crosslinked thermoset resin produced according any of the methods of the present invention described herein.

In another aspect, the present invention relates to a composite comprising: (i) a crosslinked thermoset resin produced according any of the methods of the present invention described herein; and (ii) a natural fiber, a synthetic fiber, or a particulate plant material.

In another aspect, the present invention relates to an adhesive comprising a crosslinked thermoset resin produced according any of the methods of the present invention described herein.

In another aspect, the present invention relates to a nanofiber membrane comprising: (i) a crosslinked thermoset resin produced according any of the methods of the present invention described herein; and (ii) a nanofibrillated natural fiber, a nanofibrillated synthetic fiber material, or natural whiskers.

Methods of making composites, adhesives, nanofiber membranes, and other products from the crosslinked thermoset resin of the present invention are known in the art. See, e.g., U.S. Patent Application Publication No. US2007/0148339 to Wescott et al., U.S. Pat. No. 6,306,997 to Kuo et al., U.S. Pat. No. 6,518,387 to Kuo et al., and U.S. Pat. No. 8,541,001 to Netravali et al., the disclosures of which are incorporated by reference herein in their entirety. While none of these references describes, teaches, suggests, or contemplates the presently disclosed inventions, they provide supplementary disclosure of certain methods, techniques, products, reagents, etc., that can be incorporated into aspects of the present disclosure.

Suitable methods for combining a crosslinked thermoset resin with a nanofibrillated natural fiber, a nanofibrillated synthetic fiber material, or natural whiskers are known. For example, any nanofibrillated cellulose can be used, and such are known in the art. More particularly, as provided herein, the present disclosure describes illustrative examples of methods of fabricating soy protein and wheat gluten based nanofiber membranes. Further, as provided herein, in various embodiments, the nanofiber crosslinking has been carried out using a plant based crosslinker. The crosslinking can improve the material properties, decrease moisture sensitivity and increase the useful life.

With respect to the fabrication of nanofiber membranes in accordance with the present disclosure, one of ordinary skill can use such techniques as electrospinning Electrospinning process is a simple low-cost method that has been used to produce nanofibers and nanofiber based membranes with very high specific surface area and tunable porous structures (Greiner et al., *Angew. Chem. Int. Edn. Engl.*, 2007, 46, 5670-5703). Electrospun membranes have been studied and developed because they hold considerable promise for realizing the advantages of nanostructured materials (D. V. H. Thien et al., *J. Mater. Sci.*, 2013, 48, 1640-1645; X. Liu et al., *Adv. Sci. Technol.*, 2008, 57, 125-130; H. L. Lin et al., *J.*

*Membrane Sci.*, 2010, 365, 114-122; R. S. Barhate et al., *J. Membrane Sci.*, 2007, 296, 1-8; W. Cui et al., *Sci. Technol. Adv. Mater.*, 2010, 11, 1-11; R. S. A. Hosseini, et al., *Curr. Nanosci.*, 2013, 9, 423-433; and S. Tao, et al., *J. Mater. Chem.*, 2007, 17, 2730-2736). In many cases the nanofibers can be made of green polymers as well. Electrospun biobased materials and techniques involved therewith are known in the art and can be adopted to the crosslinked thermoset resins of the present disclosure. Many studies of electrospun biobased materials are based on polypeptide-based materials such as silk fibroin, collagen, chitosan, etc. (H. Cao, et al., *J. Mater. Sci.*, 2013, 48, 150-155; B. M. Min et al., *Biomaterials*, 2004, 25, 1289-1297; Z. G. Chen et al., *Acta Biomater.*, 2010, 6, 372-382; B. Dhandayuthapani et al., *J. Biomed. Mater. Res. B Appl. Biomater.*, 2010, 94, 264-272; G. B. Yin et al., *J. Biomed. Mater. Res. A*, 2010, 93, 158-163; and D. Yang et al., *Carbohydr. Polym.*, 2007, 69, 538-543). Most of these materials are expensive and hence they are used only in niche biomedical applications rather than mass-scale commodity type applications (D. B. Khadka et al., *Nanomedicine*, 2012, 8, 1242-1262). Thus, as provided in the present disclosure, substituting these materials with inexpensive plant based proteins can provide the means for overcoming some of the cost challenges and can also expand their applications.

For example, with respect to one embodiment, soybean can be used as the source of the resin. As is known in the art, soybean is one of the most abundant crops grown in the world and the protein derived from it is available commercially in three different forms: soy protein isolate (SPI), soy protein concentrate (SPC) and defatted soy flour (SF) which contain about 90, 70 and 52% protein, respectively. The rest is carbohydrates, minerals, ash and moisture. Of all these forms, SF is the least expensive (about $0.50/kg) variety. Further, as provided in the present disclosure, a simple acid-wash process can be used to increase the protein content of SF to the level of about 70% found in SPC (H. Wang et al., *JAOCS*, 2004, 81, 713-717). This method is based on precipitating the protein at its isoelectric point (pH 4.5), in water, and then removing most of the soluble non-protein constituents. These constituents commonly include water soluble and some low molecular weight nitrogenous substances and minerals.

Gluten is another plant derived material which contains high percentage of protein and is relatively inexpensive (about $0.90/kg). Therefore, in various embodiment of the method of the present disclosure, gluten can be used at least as a source for protein. Gluten is a composite formed from several different proteins and is found most commonly in wheat and other related grains, such as barley and rye. Gluten can be defined as the rubbery mass that remains when wheat dough is washed to remove starch granules and water-soluble constituents. Depending on the thoroughness of washing, the dry solid contains 75-85% protein and 5-10% lipids; most of the remainder is starch and non-starch carbohydrates. They are unique in terms of their amino acid compositions, which are characterized by high contents of glutamine and proline and by low contents of amino acids with charged side groups (H. Wieser, *Food Microbiol.*, 2004, 24, 115-119).

As provided elsewhere herein, there is great interest in developing green nanofiber membranes, and the method of producing nanofiber membranes prepared by electrospinning of soy protein blends with polyvinyl alcohol (PVA), polylactid acid (PLA), zein or polyethylene oxide (PEO) have been described in the art and are adopted with respect to the present disclosure (C. Yao et al., *J. Appl. Polym. Sci.*, 2007, 30, 380-385; M. Phiriyawirut et al., *Adv. Mater. Res.*, 2008, 55-57, 733-736; A. C. Vega-Lugo et al., *Food Res. Int.*, 2009, 42, 933-940; and D. Cho et al., *Polymer Degradation and Stability*, 2012, 97, 747-754). However, disintegration of the nanofiber membranes in water is one of their biggest disadvantages. In accordance with the present disclosure, this limitation can, however, be overcome by crosslinking of the polymer. Crosslinking has been the most commonly used technique to improve resistance to water as well as to improve the physical properties of polymers. Crosslinking is the process of chemically joining two or more molecules by a covalent bond. Crosslinking agents (or crosslinkers) are molecules that contain two or more reactive groups capable of chemically reacting with specific functional groups on proteins or other molecules. Despite the complexity of protein structure that contains several different amino acids, only a small number of protein functional groups comprise selectable targets for practical bioconjugation method (S. S. Wong et al., *National Institutes of Health*; CRC Press, USA, 1991). As described elsewhere herein, just four protein functional-group targets account for most of the crosslinking modifications. These include the following: (a) primary amines (—$NH_2$); (b) carboxyls (—COOH); (c) hydroxyl (—OH); and (d) sulfhydryls (—SH). For each of these protein functional groups there exist one to several types of reactive groups that are capable of reacting with them and have been used as the basis for synthesizing crosslinking reagents (S. S. Wong et al., *National Institutes of Health*; CRC Press, USA, 1991).

As described herein, the present invention provides a unique method for using an intrinsic and benign crosslinking agent to make the crosslinked thermoset resins of the present invention. Most commonly used crosslinkers for amine groups are bi-functional compounds, such as glutaraldehyde and glyoxal. Several papers have described crosslinking reactions in protein based resins with glutaraldehyde or glyoxal (S. K. Park et al., *JAOCS*, 2000, 77, 879-884; and S. Chabba et al., *J. Mater. Sci.*, 2005, 40, 6275-6282). Both of these crosslinkers, however, are toxic and inappropriate from the environmentally-friendly point of view, and hence green crosslinkers as provided in the present disclosure are preferred. The oxidized sugars (OS) have been found to be useful in such cases and could be regarded as green crosslinking agents for soy and other protein based resins (T. Ghosh-Dastidar et al., *Green Chem.*, 2013, 15, 3243-3251; A. M. Velarde et al., *J. Mol. Catal. A: Chem.*, 2000, 157, 225-236; and M. Comotti et al., *Adv. Synth. Catal.*, 2005, 348, 313-316).

Oxidized sugars are carbohydrates that are oxidized by weak oxidizing agents and generate compounds containing reactive aldehyde or carboxyl groups (T. Ghosh-Dastidar et al., *Green Chem.*, 2013, 15, 3243-3251). The aldehyde groups in OS can crosslink the nucleophilic amino groups in soy or other protein based resins utilizing the Maillard reaction (R. Ikan, *The Maillard reaction, Consequences for the Chemical and Life Sciences*; John Wiley and Sons Ltd., England, 1996). Since OS can have multiple aldehyde groups, they can react with different protein molecules forming a crosslinked resin system. One of the major advantages of this reaction is that it can be carried out in an aqueous medium. The reactive aldehyde group of OS reacts with the nucleophilic amino groups of the amino acids, and forms bonds responsible for non-disintegration of soy protein based resin. The influences of sugar and a thermal treatment process on the properties of a polyethylene/chitosan membrane have been also been provided (J. W. Wang et al., *J. Biomater. Sci. Polym. Ed.*, 2003, 14, 119-137). With increasing treatment temperature, the crosslink density can be increased.

In accordance with various aspects of the present disclosure, there is provided fabrication and green crosslinking of very inexpensive protein based nanofiber membrane focusing on the use of SF. In a particular embodiment, SF can be used, with SF being the least expensive source of the soy protein with the lowest content of protein. However, other plant flours can be used as well. In particular embodiments, an acid-wash process can be used to increase the protein content of SF to the level of 70% found in commercial SPC. This 'purified soy flour' (PSF) can be used as the major constituent for fabrication of nanofiber membrane. Key factors which: (i) play significant role in electrospinning process of protein based polymer solution and (ii) influence the morphology of resulted nanofiber membrane are described herein. As provided in the experimentals of the present disclosure, crosslinking protein nanofiber based membranes by using a green crosslinking agent to increase its moisture resistance and hence the durability can be employed. Sucrose was shown to oxidize with $H_2O_2$ and can be used to synthesize OS and was confirmed to be a good crosslinking agent for protein based nanofiber membrane using FTIR and sol-gel test. Finally, crossliking quality of protein based material by OS was compared with the properties of glyoxal crosslinked membranes. Such 'green' nanofiber membranes may be used for filtration of dust, bacteria or viruses as well as in biotechnology applications (D. Lubasova et al., *J. Nanosci. Nanotech.*, 2013—In press).

EXAMPLES

The following examples are intended to illustrate particular embodiments of the present invention, but are by no means intended to limit the scope of the present invention.

Example 1

Soy Flour Based Thermoset Resin without the Use of External Crosslinker

A novel water based reaction scheme was developed to crosslink the protein from soy flour (SF), without using any external crosslinker. Soy flour, which contains about 55% protein and 32% carbohydrate and is the least expensive commercially available soy protein variety, was used for this research. Sugars and protein from the SF were separated using a simple lab based filtration technique. Sugars were then oxidized using $H_2O_2$, a benign oxidizing agent to obtain aldehyde and carboxyl groups. The oxidized sugars containing those groups were then used to crosslink the reactive groups present the protein separated from SF, mainly utilizing Maillard type chemistry. The resulting crosslinked (thermosetting) soy protein resin had enhanced mechanical, thermal properties and reduced moisture absorption. When reinforced with strong microfibrillated cellulose they can produce fully sustainable and biodegradable green composites. The novel scheme developed here may be extended for preparing biobased plastics with enhanced properties by crosslinking natural flours with similar composition (soluble sugars and protein).

Experimental Methods

Materials

SF and SPI were obtained from Archer Daniels Midland Co. (Decatur, Ill.). Sucrose and glucose were purchased from VWR and Sigma Aldrich, respectively. Analytical grade hydrochloric acid (HCl), sodium hydroxide (NaOH) and 30% hydrogen peroxide ($H_2O_2$) were obtained from VWR.

Filtration of SF

As mentioned earlier, the first step involved separating the soy protein and soluble sugars (fructose, glucose, sucrose, raffinose and stachyose) present in SF using a lab based filtration technique. To achieve this, SF was dissolved in water (10 times by weight of SF) by magnetic stirring at room temperature. The solution pH was changed from about 7 to 4.5 using HCl solution. Soy proteins become insoluble in water at pH 4.5, their isoelectric point. As a result, the protein molecules precipitate but the sugars remain dissolved and thus can be separated easily by filtration. The retentate, consisting of higher protein content, was rinsed twice with deionized water to remove any remaining sugars and used as PSF for further crosslinking reactions. The filtrate, soy flour extract (SFE), consisting of sugars in water was collected and used for oxidation reaction. Both PSF and SFE were used as obtained for further processing.

Oxidation of Sugars with $H_2O_2$

The SFE sugars ($\approx$16 g) obtained by the filtration of 50 g SF were oxidized using 50 mL of 30% $H_2O_2$ at pH 2.0 (using HCl). $H_2O_2$ was added directly to the SFE without further processing. The oxidation reaction was carried out overnight at 60° C. to ensure as complete oxidation as possible. In the present study glucose and sucrose were separately oxidized, using acidified $H_2O_2$ (pH=2), to confirm the oxidation reactions and to confirm crosslinking with protein (SPI).

Preparation of SPI and Crosslinked SPI Resin Films

SPI, which contains over 90% protein, was crosslinked with oxidized sucrose, as a preliminary study, to understand and confirm the reactions between proteins and oxidized sugars. To fabricate pure SPI films SPI was denatured in water at 70° C. and pH of 10 which led to the formation of a smooth resin due to opening of the protein chains. The denatured SPI was cast onto Teflon® coated glass plates to obtain control films. To fabricate crosslinked SPI films it was denatured and crosslinked by reacting the amine and hydroxyl groups with oxidized sucrose. The pH value dropped on adding the acidic oxidized sucrose solution to SPI which was adjusted back to pH 10 by adding necessary amount of NaOH to the reaction mixture. Significant effervescence generated on adding the oxidized sucrose to soy protein was allowed to die down to form a smooth crosslinked SPI resin which was cast into films on Teflon® coated glass plates. The films were dried at 40° C. for 36 hours, washed thoroughly in water and dried again at 40° C. for 24 hrs using a convection oven, to remove all the water. This stage is referred to as the precuring of resins when the resins are partially crosslinked. To complete the crosslinking process the films were further cured by hot pressing at 120° C. for 20 min (at 1 MPa pressure) leading to complete crosslinking as well as formation of a smooth film for characterization.

Preparation of SF Resin and Crosslinked SF Resin

SF was denatured at 70° C. and pH 10 and cast into a film following the same procedure as SPI resin based films mentioned in the previous paragraph. To make crosslinked SF resin the protein was first extracted from SF by the filtration technique described earlier. The purified protein (PSF) obtained from SF filtration was diluted in water and denatured at 70° C. and pH of 10 to open up the molecules and expose the reactive functional groups. At this pH the denatured protein was allowed to react with the oxidized SFE, the pH was adjusted to 10 by adding NaOH. As before, the films were cast on Teflon® coated glass plates. As explained earlier, this stage is referred to as the precuring of resins when the resins are partially crosslinked. To complete the crosslinking process the films were further cured at 120° C. for 20 min. This crosslinked resin will henceforth be referred to as crosslinked SF resin which had essentially the same constituents as the original SF (protein and sugars), the only change being that the sugars were oxidized to aldehydes and carboxylic acids. The oxidized sugars reacted with the amine and hydroxyl groups to crosslink the proteins. The SF and crosslinked SF films were fabricated, washed thoroughly in water, dried and conditioned before characterization using the same procedure as described for SPI films, to compare the properties of SF resin and crosslinked SF resin.

To fabricate films for tensile testing, microfibrillated cellulose (MFC) (5% dispersion in water by wt.) was added to both SF resin and precured SF resin. This was done for ease of film formation and fabrication of relatively defect free, ductile films needed for tensile testing. Typically, for the fabrication of soy protein based thermoplastic resin, glucose and sucrose (polyol) are used as plasticizers (J. T. Kim and A. N. Netravali, *Journal of Agricultural and Food Chemistry*, 2010, 58, 5400-5407). The precured SF (with 5% MFC) was cured at 120° C. and 20 minutes followed by a thorough washing. The washing was important to remove unreacted sugar molecules which can plasticize the films as well as allow moisture absorption. The incorporation of MFC helped in the drying process by preventing defect formation, wrinkling and curling of the films. Adding MFC also increased the tensile properties of the resin films by reducing the brittleness and increasing the Young's modulus. Conditioned (at 65% relative humidity, 21° C. for 3 days) composite sheets were cut into rectangular specimens of 10 mm×50 mm dimensions for tensile testing. The rectangular specimens were also cut in random directions from the original film to assess the isotropicity of the composite films.

Chemical Characterization

Attenuated total reflectance—Fourier transform infrared (ATR-FTIR) analysis: ATR-FTIR spectra were collected using a Nicolet Magna 560 FTIR spectrometer with a split pea accessory for ATR. Each scan was an average of 150 scans recorded from 4000 $cm^{-1}$ to 550 $cm^{-1}$ wavenumbers at a resolution of 4 $cm^{-1}$.

Film Characterization

Film Color: The color of the films, which changed due to crosslinking through Maillard reaction, was measured with Hunterlab Colorimeter (Ultrascan Pro., Hunter Associated Laboratory Inc., Reston, Va.); L, a and b values were measured. The ranges of the three color coordinates (L, a, b) were 0 black to 100 white, – greenness to + redness, and – blueness to + yellowness, respectively. Standard values refer to the white calibration plate (L=94.47, a=–0.81, b=–0.86) (S. K. Park et al., *Journal of the American Oil Chemists' Society*, 2000, 77).

Sol-gel Test: A pre-weighed amount of resin (pure and crosslinked) specimens (conditioned at 21° C. and 65% RH for 3 days) were immersed separately in 50 ml distilled water in a glass bottle and placed on a platform shaker (Innova™ 2300, New Brunswick Scientific Inc., New Brunswick, N.J.) at 80° C. and 100 rpm for 3 days. The contents of the bottle were washed/filtered using a microfiber based fabric filter. The gel residue on the fabric filter was then air-dried at 40° C. for 24 hrs and subsequently conditioned (as per ASTM) at 65% RH and 21° C. for 3 days.

Thermogravimetric Analysis (TGA): Pure SF and crosslinked SF resin specimens were scanned from 25° C. to 600° C. using a thermogravimetric analyzer (TGA-2050, TA Instruments, Inc., New Castle, Del.) at a rate of 10° C./min in a nitrogen atmosphere to characterize their thermal stability and degradation behavior. At least 3 specimens were tested to obtain average property values.

Tensile Properties: Tensile properties of the SF and crosslinked SF resin sheets, both in the form of composites containing 5% MFC, were characterized in accordance with ASTM D 882-97. At least five thickness measurements of the films were taken along the length of each specimen and the average of these values was used for calculating the fracture stress and Young's modulus values. The tests were performed on an Instron universal tensile tester, model 5566, at a strain rate of 2 $min^{-1}$ and a gauge length of 30 mm. At least 5 specimens were tested to obtain average properties. The fracture surfaces of crosslinked SF resin were observed under FEI Nova 2300 scanning electron microscope (SEM). The fractured specimens were sputter coated with gold to get good conductivity.

Results and Discussions

Structure, Reactions and Mechanism

Figure 2:
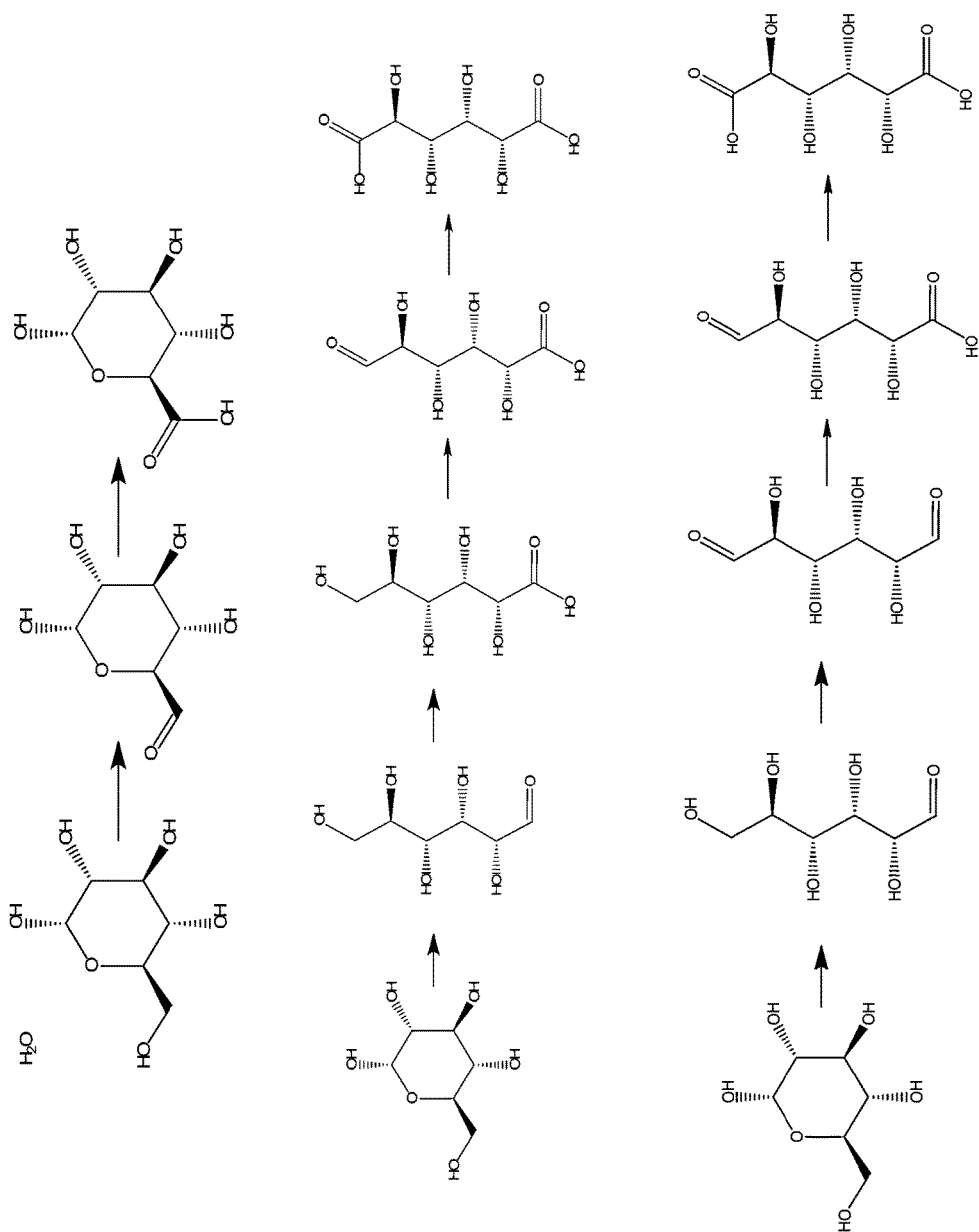
FIG. 2: Scheme of proposed reactions for oxidation of glucose.
Figure 3:
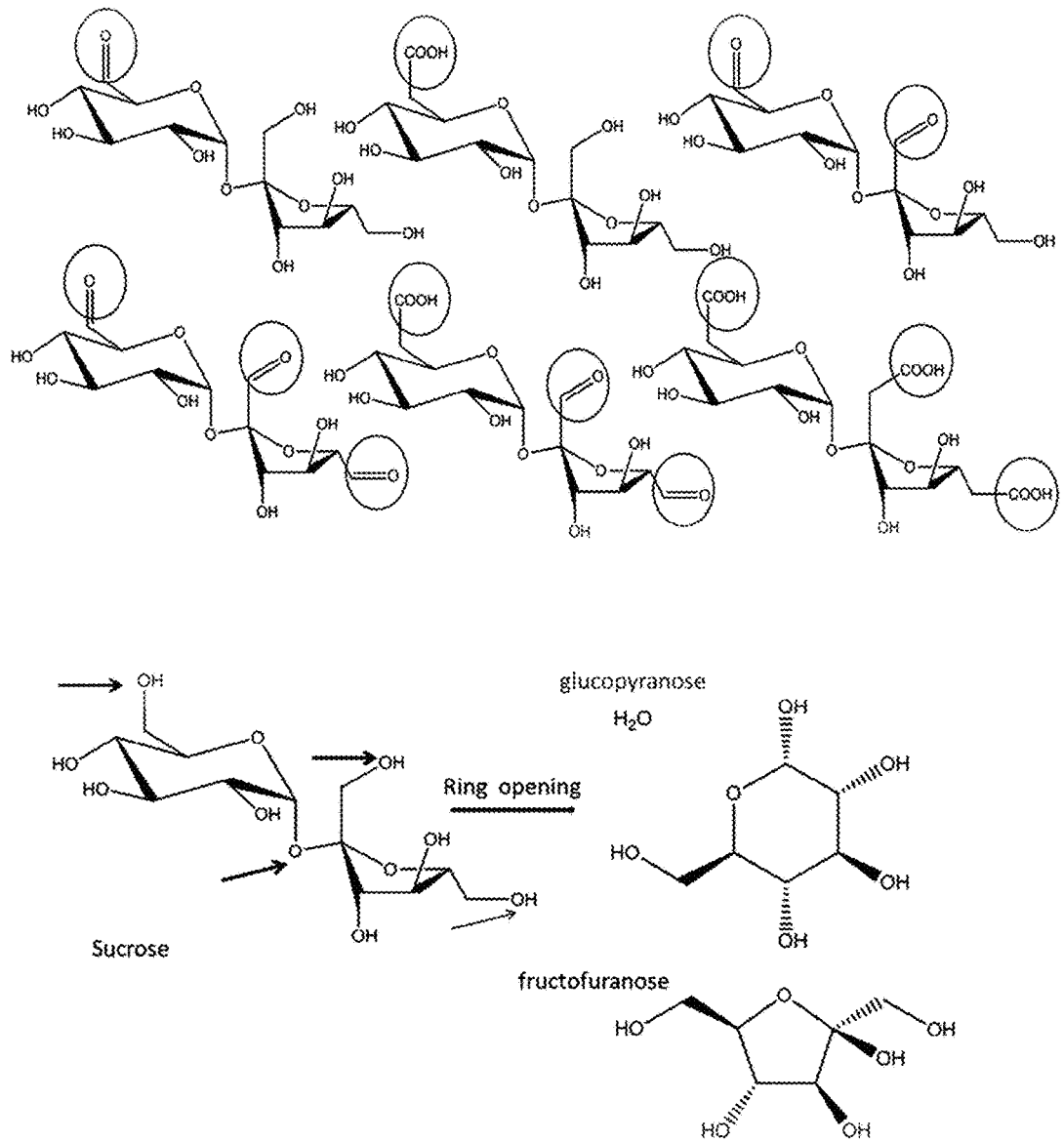
FIG. 3: Scheme of proposed reactions for oxidation of sucrose.

In the present research acidified $H_2O_2$, a strong but water based and environmentally benign oxidizing agent, was used for oxidation of sugars present in the SFE. Prior to that, oxidation of commercially available glucose and sucrose was studied as model reactions. Oxidation of sugars can lead to formation of different oxidation products as proposed in the schemes of FIG. 2 and FIG. 3 for glucose and sucrose, respectively. Previous research on the oxidation of carbohydrates, in fact, indicated that the oxidation of even simple sugars such as D-glucose can have different reaction mechanisms and products depending on the pH, temperature, concentration and the type of catalyst used in the reaction (M. Comotti et al., *Adv. Synth. Catal*, 2005, 348; D. Dewit et al., *Carbohydrate Research*, 1992, 226, 253-260; and A. M. Velarde et al., *Journal of Molecular Catalysis A: Chemical*, 2000, 157). Typical oxidants for carbohydrates (sugars) include $CrO_3$, $KMnO_4$, $HNO_3$, $HIO_6$ which are highly oxidizing but toxic in nature. Periodates have been previously used for selective oxidation of the vicinal diols in sugars (D. Dewit et al., *Carbohydrate Research*, 1992, 226, 253-260; and C. B. Barlow et al., *Chemical Communications*, 1966, 268-269). Often metal catalysts such as gold, titanium or iron have been used for clean and efficient oxidation reactions (M. Comotti et al., *Adv. Synth. Catal*, 2005, 348; and A. M. Velarde et al., *Journal of Molecular Catalysis A: Chemical*, 2000, 157). For example, titanium containing zeolites were used by Velarde et al. (A. M. Velarde et al., *Journal of Molecular Catalysis A: Chemical*, 2000, 157) to catalyze oxidation of D-glucose with 30% $H_2O_2$ as the oxidant. In their study D-glucose was converted to gluconic acid, glucuronic acid, tartaric acid, glyceric acid, glycolic acid via oxidation of intermediate aldehydes as a result of the catalytic oxidation (A. M. Velarde et al., *Journal of Molecular Catalysis A: Chemical*, 2000, 157). Dewit et al. (*Carbohydrate Research*, 1992, 226, 253-260) oxidized sucrose by using periodate in aqueous dimethyl formamide (DMF). At pH of 7 and a temperature of 95° C. dialdehydes were selectively formed by double oxidation of the glucose ring. The reaction was thought to proceed via formation of a cyclic ester intermediate. A 1:1 mixture of glucose and fructose were formed at pH of 5 to 7 and 25° C. The pH and temperature as well as presence of water influence the regioselectivity of the sucrose oxidation. TEMPO (2,2,6,6-tetramethylpiperidin-1-yl) oxidanyl mediated hypochlorite oxidation system has been used for sucrose which leads to the selective oxidation of primary alcohol to carboxylic acid group (P. L. Bragda et al., *Topics in Catalysis*, 2004, 27, 1-4). An aqueous solution of sucrose treated with sodium hypochlorite (NaOCl, 2.2 equivalents) in the presence of sodium bromide and TEMPO at pH of 10 and 5° C. leads to the formation of sodium sucrose tricarboxylate. It has been shown that the reaction of isomaltose with $H_2O_2$ under acidic conditions is hard to control and can lead to partially degraded products due to chain scission (S. P. Trombottoa et al, *Topics in Catalysis*, 2004, 27, 1-4). Under controlled acidic medium, however, the reaction leads to essentially one product, carboxymethyl α-D-glucopyranoside (α-CMG) (S. P. Trombottoa et al, *Topics in Catalysis*, 2004, 27, 1-4). The reaction of palantiose with excess hydrogen peroxide at pH of 2 without any catalyst or at pH of 4 with sodium tungstate as catalyst, both reactions carried out at 80° C., resulted in the formation of carboxymethyl α-D-glucopyranoside (α-CMG) (S. P. Trombotto et al., *Tetrahedron Letters*, 2000, 41, 8273-8277). It was also shown in these studies that the oxidation of fructose was easier than the oxidation of palantiose itself. From the previous research results it was quite clear that a range of oxidation products was possible for oxidation of sugar molecules. It was difficult to predict and characterize all reaction products of the SFE oxidation owing to the wide range of possible reaction products and mechanisms. While characterization of the oxidation products was not the main intent of this research, it was postulated that both aldehydes and carboxylic acids were produced as a result of oxidation of the different sugars present in SFE.

Both aldehydes and poly carboxylic acids have the potential to react with different functional groups available in soy protein and crosslink them (X. Huang and A. N. Netravali, *Biomacromolecules*, 2006, 7, 2783-2789; P. Lodha and A. N. Netravali, *Polymer composites*, 2005 26, 647-659; and S. B. M. Yasir et al., *Food Chemistry*, 2007, 104, 1502-1508). Yasir et al. (*Food Chemistry*, 2007, 104, 1502-1508) showed that soy protein can be crosslinked with formaldehyde, gluteraldehyde (GA) and glyceraldehyde through Maillard reaction, which leads to considerable reddish coloration of the crosslinked product. Bifunctional aldehydes such as GA react with the basic amino acids such as lysine, arginine and histidine in soy protein and provide intra- and/or intermolecular crosslinking. Chabba and Netravali (*Journal of Material Science*, 2005, 40, 6263-6273) prepared biodegradable resin by crosslinking SPC with GA. They found the Young's modulus of the SPC resin increased by 35% after crosslinking. At the alkaline condition (pH 10), the soy protein molecules can be denatured and open (unfolded) form, making it easy to process (J. T. Kim and A. N. Netravali, *Journal of Agricultural and Food Chemistry*, 2010, 58, 5400-5407). Adding polycarboxylic acids such as Phytagel® to SPI have also been shown to improve their tensile properties by forming an interpenetrating network (IPN) structure (X. Huang and A. N. Netravali, *Biomacromolecules*, 2006, 7, 2783-2789; and P. Lodha and A. N. Netravali, *Polymer composites*, 2005 26, 647-659). However, Phytagel® which is composed of glucuronic acid, rhamnose and glucose is also capable of reacting with the amino acids in soy protein (Id.). Glucuronic acid contains carboxylic acid groups which react with the amine, hydroxyl and carboxyl groups present in soy protein to form amide, ester and anhydride linkages respectively (Id.). Similarly, the aldehydes and polycarboxylic acids produced as a result of SFE oxidation react with the polar amino acids in soy proteins (aspartic acid, threonine, serine, glutamic acid, glycine, tyrosine, histidine, lysine and arginine). The most probable reaction products between oxidized sugars and proteins are imines, amides, esters and anhydrides. ATR-FTIR spectroscopy was used to confirm the reactions.

Figure 4:
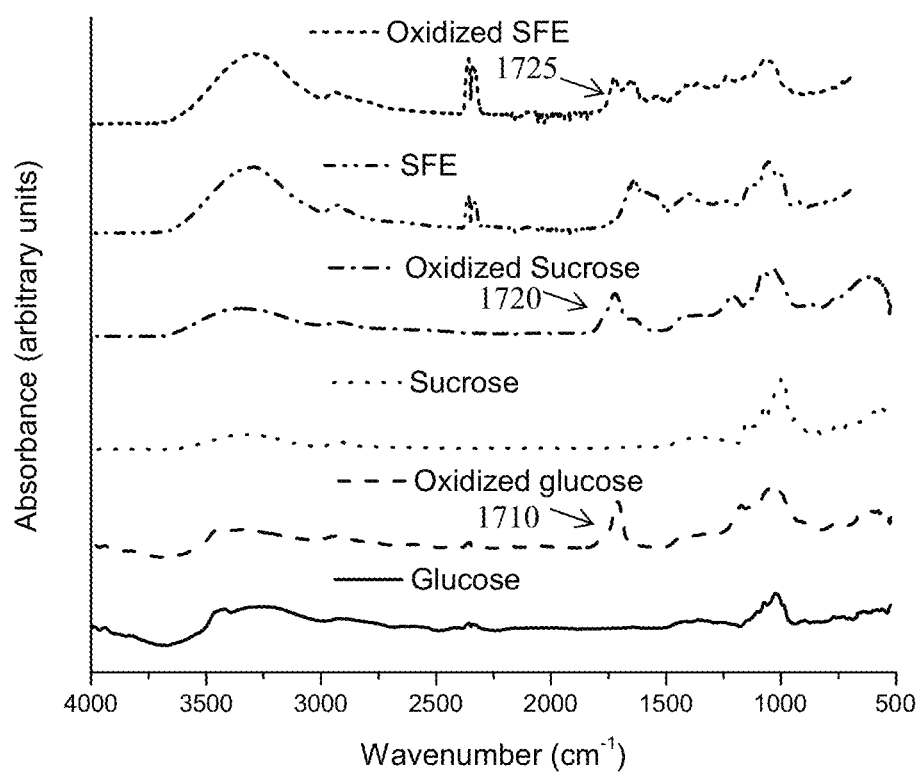
FIG. 4: ATR-FTIR spectra of sugars (glucose, sucrose and SFE) and oxidized sugars.

FIG. 4 shows ATR-FTIR spectra of sugars (glucose, sucrose and SFE) and oxidized sugars. In the FTIR spectra all oxidized sugars show a carbonyl peak at 1710 cm$^{-1}$ (glucose), 1720 cm$^{-1}$ (sucrose) and 1725 cm$^{-1}$ (SFE). These peaks correspond to carbonyl peaks from oxidation of the primary alcohols to aldehydes and/or carboxylic acids. These peaks are absent in the unreacted sugars which do not have carbonyl groups. This confirms the oxidation of sugars with acidified $H_2O_2$. The exact nature of the carbonyl peak (aldehyde or carboxylic acid or both) could not be identified from the ATR-FTIR spectra. The formation of carboxylic acids by sucrose and glucose oxidation was also confirmed by monitoring a sharp change in pH to below 2. However, as mentioned earlier, both aldehyde and carboxyl groups can react with the amines, hydroxyl and carboxyl groups in the proteins to produce imines, amides, esters and anhydrides and thus crosslink it.

Figure 5:
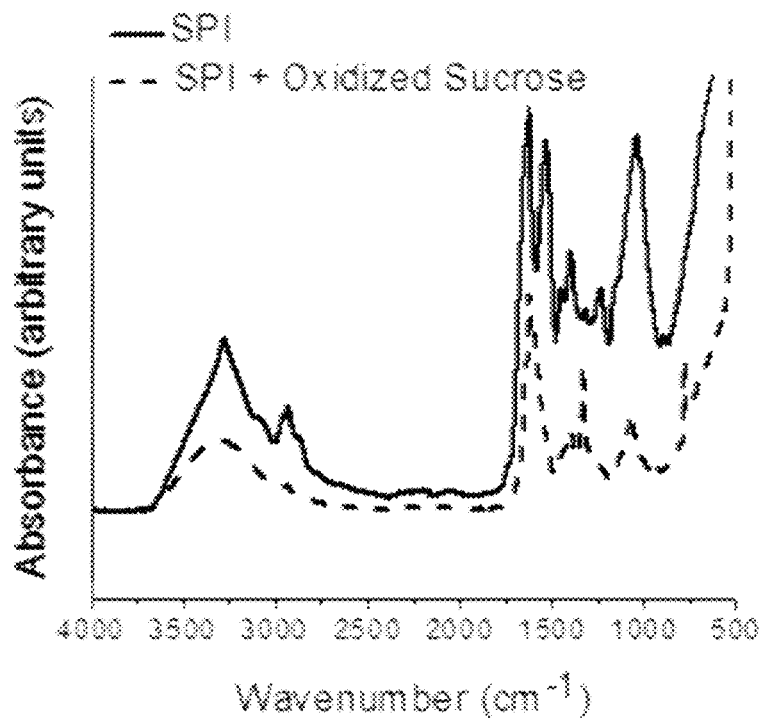
FIG. 5: ATR-FTIR spectra of SPI and SPI+oxidized sucrose (crosslinked SPI).

FIG. 5 shows ATR-FTIR spectra of SPI and SPI+oxidized sucrose (crosslinked SPI). A typical soy protein spectrum shows three major peaks at 1638, 1537, and 1238 cm$^{-1}$, which are assigned to C—O stretching (amide I band), N—H deformation (amide II band), and C—N stretching and N—H vibration (amide III band), respectively, as shown in FIG. 5 (J. T. Kim and A. N. Netravali, *Journal of Agricultural and Food Chemistry*, 2010, 58, 5400-5407). The carboxylic acids formed due to oxidation of glucose or sucrose can crosslink proteins via formation of anhydride, ester or amide linkages (X. Huang and A. N. Netravali, *Biomacromolecules*, 2006, 7, 2783-2789; and P. Lodha and A. N. Netravali, *Polymer composites*, 2005 26, 647-659). No ester peak was detected at 1720-1730 cm$^{-1}$ for SPI crosslinked with oxidized sucrose indicating that the crosslinking took place without the formation of an ester linkage. Because of the large number of amide linkages already present in the soy protein it was not possible to detect the formation of any additional amide bonds. Formation of imine linkages by the reaction of amine groups with aldehyde (Maillard reaction) are also hard to detect in the ATR-FTIR spectra due to overlap of several peaks in the fingerprint regions. However, the formation of imine linkage can be detected by observing the color change in the specimen as explained later.

Figure 6:
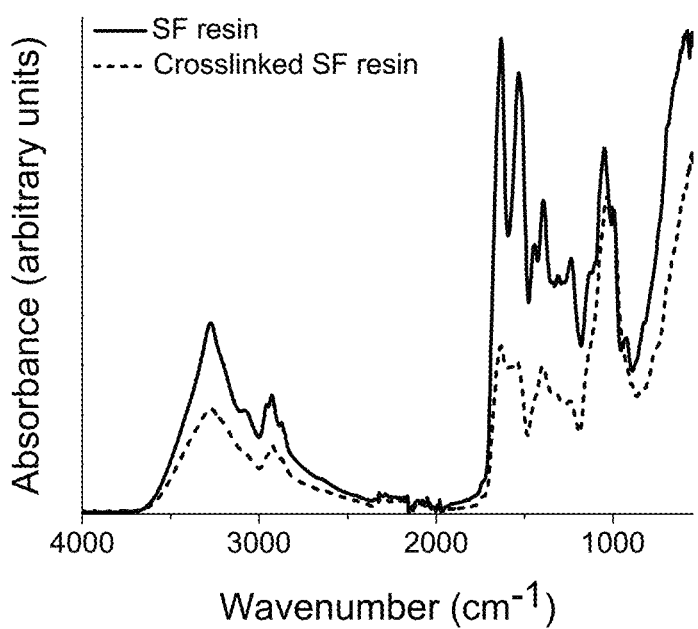
FIG. 6: ATR-FTIR spectra of SF resin and crosslinked SF resin.

The ATR-FTIR spectra of SF resin and crosslinked SF resin are presented in FIG. 6. The ATR-FTIR spectrum for SF in FIG. 6 shows another major peak at 1049 cm$^{-1}$, which is assigned to C—O stretching, indicating the presence of sugar molecules. This peak is not present in the ATR-FTIR spectrum for soy proteins (SPI) which do not have significant amount of sugars. As mentioned earlier it was difficult to characterize the different reactions and reaction products using ATR-FTIR owing to the wide range of possible reaction products (imines, esters and amides) and some of the groups already present in the protein. Similar difficulties have been expressed by others as well (J. T. Kim and A. N. Netravali, *Journal of Agricultural and Food Chemistry*, 2010, 58, 5400-5407; X. Huang and A. Netravali, *Compos Sci Technol*, 2009, 69, 1009-1015; X. Huang and A. N. Netravali, *Journal of Macromolecular Science, Part A: Pure and Applied Chemistry*, 2008, 45, 899-906; X. S. Huang and A. Netravali, *Compos Sci Technol*, 2007, 67, 2005-2014; S. Chabba, G. F. Matthews and A. N. Netravali, *Green Chemistry*, 2005, 7, 576-581; S. Chabba and A. N. Netravali, *J. Mater. Sci.*, 2005, 40, 6275-6282; A. N. Netravali, in *Biodegradable Natural Fiber Composites*, ed. R. S. Blackburn, Woodhead Publishing Limited, Cambridge, 2005, pp. 271-309; P. Lodha and A. N. Netravali, *Composites Science and Technology*, 2005, 65, 1211-1225; P. Lodha and A. N. Netravali, *J. Mater. Sci.*, 2002, 37, 3657-3665; and R. Nakamura, A. N. Netravali, et al., *Fire and Materials*, 2012). However, the crosslinking could be easily confirmed using other characterization techniques including change in color, sol-gel analysis and tensile testing.

Characterization of Films

Color Test

Figure 7:
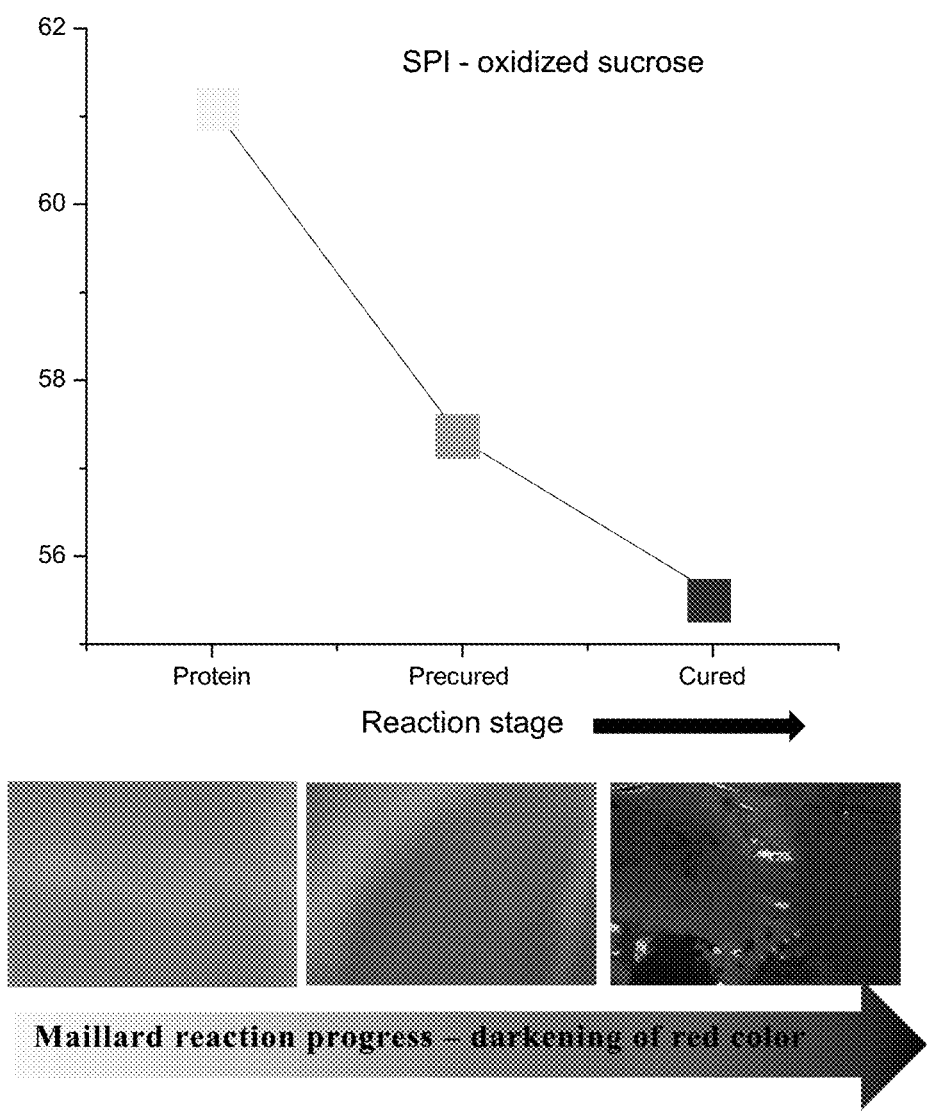
FIG. 7: Changing of color from pale yellow (beige) to dark red color with the progression in Maillard reaction between amine groups in amino acids (in SPI) and aldehyde groups in the oxidized sucrose.

Maillard reaction which takes place between the amine group in protein and the aldehyde group of oxidized sugars or SFE is responsible for the red coloration of the crosslinked protein. FIG. 7 shows change in color from pale yellow (beige) to deep red color with the progression in Maillard reaction. This color change has been noted by many other researchers as well (S. Chabba and A. N. Netravali, *Journal of Material Science*, 2005, 40, 6263-6273; X. Huang and A. N. Netravali, *Biomacromolecules*, 2006, 7, 2783-2789; X. Huang and A. Netravali, *Compos Sci Technol*, 2009, 69, 1009-1015; X. Huang and A. N. Netravali, *Composites Science and Technology*, 2009, 69, 1009-1025; S. Chabba, G. F. Matthews and A. N. Netravali, *Green Chemistry*, 2005, 7, 576-581; and S. Chabba and A. N. Netravali, *J. Mater. Sci.*, 2005, 40, 6275-6282). In the Hunter color test a decrease in L value indicates increase in the deepness of the red color of the sample (S. K. Park et al., *Journal of the American Oil Chemists' Society*, 2000, 77). The effect of oxidized sugar reaction with SPI on the Hunter color values of the SPI was significant. As the reaction progressed from the unreacted to partially cured (precured) and to fully cured stage, the L value decreased indicating that the deepness of the red color increased. Identical results were observed for crosslinking of PSF with oxidized SFE (crosslinked SF resin). This confirms, qualitatively, that the aldehyde groups produced by the oxidation of SFE were reacting with the denatured PSF obtained from soy flour, i.e., the crosslinking was indeed occurring.

Sol-Gel Test

Figure 8:
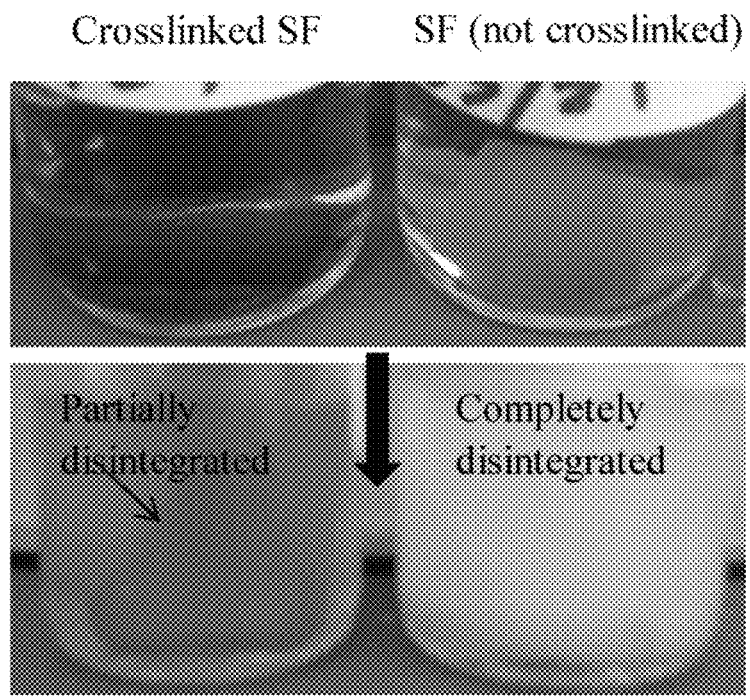
FIG. 8: Results of the sol-gel test: SF film, disintegrated, (right) and crosslinked SF, only partially disintegrated, (left).

Sol-gel test for SPI and crosslinked SPI resins showed that SPI completely disintegrated in water while crosslinked SPI resin (with oxidized glucose and sucrose) remained intact. Similar results were observed for SF resin and crosslinked SF resin. FIG. 8 shows sol-gel test results for SF film (top right) and crosslinked SF film (top left). Pure SF resin film completely disintegrated in water (bottom right) while the crosslinked SF resin film remained mostly intact (bottom left) even after being continuously shaken in water at 80° C. for 3 days. The slight disintegration of the crosslinked SF, however, did indicate that the specimens were not highly crosslinked. The gel fraction (crosslinked part) of the crosslinked SF resin was calculated to be 42% whereas the gel fraction of the pure SF was 0%. As mentioned earlier by Kim and Netravali (*Journal of Agricultural and Food Chemistry*, 2010, 58, 5400-5407) PSF contains just over 65% protein. Higher protein content of 90% and above present in SPI would obviously show higher crosslinking. This result, however, suggests that there is scope for optimization of the reaction by adjusting time, pH and controlling the oxidation of sugars to aldehydes and carboxylic acids to reach the maximum crosslinking potential. However, optimization studies are not addressed as a part of this study.

Thermogravimetric Analysis (TGA)

Figure 9:
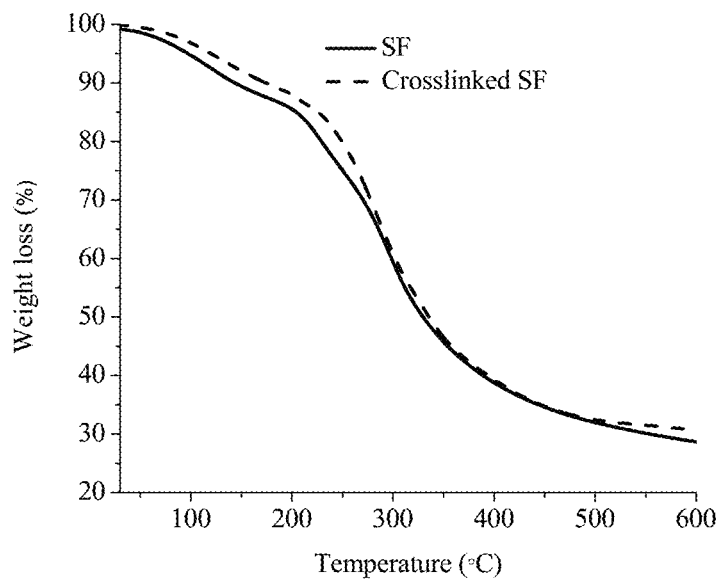
FIG. 9: TGA of SF and crosslinked SF.

TGA thermograms of SF and crosslinked SF resin specimens are presented in FIG. 9. The TGA thermograms of SF and crosslinked SF resins show that there was an increase in the initial degradation temperature of the resin from 219° C. to 233° C. after crosslinking Table 1 presents the initial degradation temperatures of SF and crosslinked SF.

TABLE 1

Initial degradation temperatures of SF and crosslinked SF.

| Specimen | Initial degradation temperature (° C.) |
|---|---|
| SF | 219 |
| Crosslinked SF | 233 |

The results confirm an increase in thermal stability of SF resin after crosslinking Chabba and Netravali (*Green Chemistry*, 2005, 7, 576-581) also reported an increase in the thermal stability after crosslinking the soy protein. The same authors also reported an increase in the initial degradation temperature of SPC from 235° C. to 270° C. after crosslinking with GA (S. Chabba and A. N. Netravali, *Journal of Material Science*, 2005, 40, 6263-6273).

Tensile Properties

Incorporation of a small amount of (5 wt %) MFC to both crosslinked and non-crosslinked SF resin films increased the flexibility and the ease of handling the films during tensile testing. Addition of MFC also eliminated the need for plasticizer (glycerol). Plasticizers such as glycerol and sorbitol absorb moisture which further decreases their glass transition temperature. This, in turn, results in lowering the Young's modulus while increasing the higher fracture strain values (A. Lopez-Rubio et al., *Carbohyd Polym*, 2007, 68, 718-727). It should be emphasized, that incorporation of small amount of MFC, instead of polyol based plasticizers, increased the fracture strain, as a result of crack bridging. Table 2 presents Young's modulus, fracture stress and fracture strain data for both SF and crosslinked SF films.

TABLE 2

Young's modulus, fracture stress and fracture strain of SF and crosslinked SF resin films.

| Specimen* | Modulus (MPa) | Fracture Stress (MPa) | Fracture Strain (%) |
|---|---|---|---|
| Soy flour | 1106 (17)** | 9.2 (28) | 1.8 (37) |
| Crosslinked soy flour | 6375 (56) | 58 (39) | 2.7 (33) |

*5% MFC dispersion was added to both SF and crosslinked SF resin for fabricating relatively defect free films and ease of handling during mechanical testing.
**Numbers in parenthesis are coefficient of variation (%)

Figure 10:
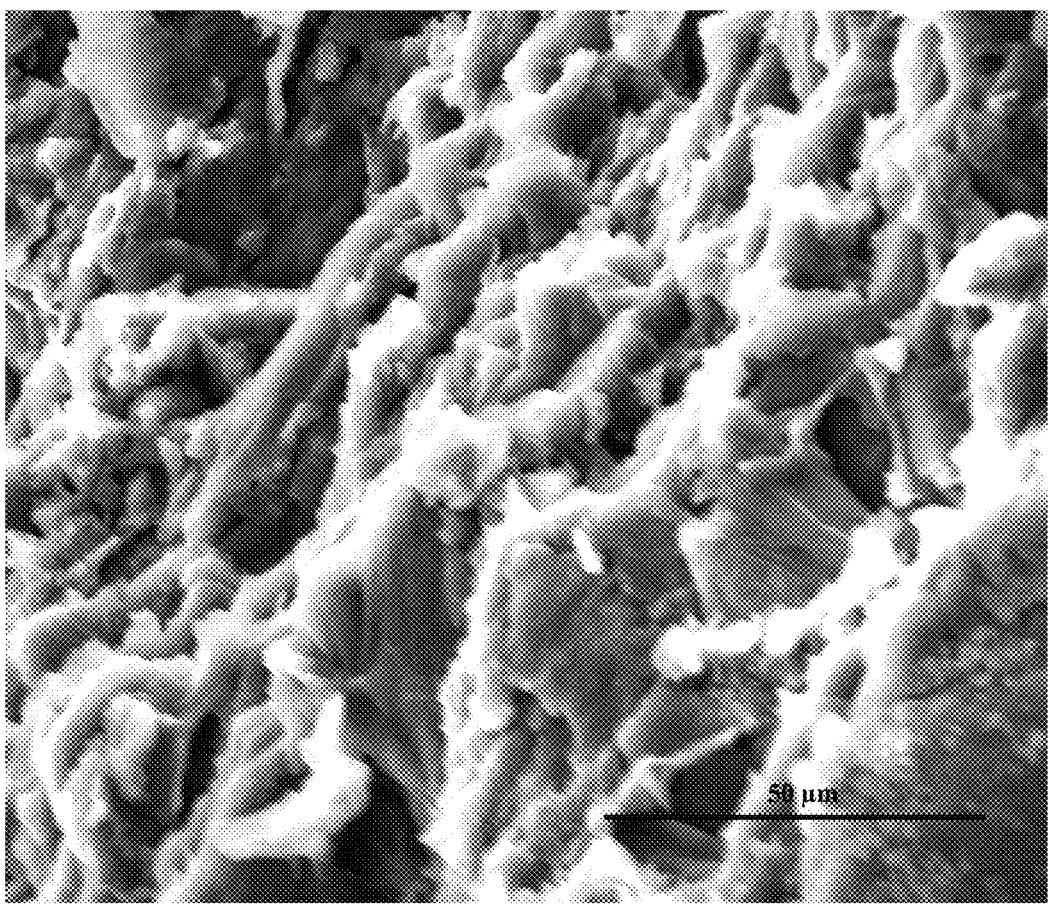
FIG. 10: SEM image showing fracture surface of crosslinked SF.

It can be seen from these data that both Young's modulus and fracture stress increase after crosslinking the films as can be expected. Significantly higher Young's modulus of 6375 MPa and fracture stress of 58 MPa, after crosslinking, compared to 1106 MPa and 9.2 MPa before crosslinking, clearly indicate that the crosslinking was successfully carried out. These results are similar to the previous literatures where effects of crosslinking on the tensile properties of the polymer films have been studied (X. Huang and A. N. Netravali, *Biomacromolecules*, 2006, 7, 2783-2789; X. Huang and A. Netravali, *Compos Sci Technol*, 2009, 69, 1009-1015; P. Lodha and A. N. Netravali, *Composites Science and Technology*, 2005, 65, 1211-1225; and P. Lodha and A. N. Netravali, *Polymer composites*, 2005 26, 647-659). Chabba and Netravali (*Journal of Material Science*, 2005, 40, 6263-6273) reported the crosslinking of SPC with 40% glutaraldehyde and the crosslinked SF showed a Young's modulus of 500 MPa. In another study, gellan which formed interpenetrating network (IPN) by strong hydrogen bonding and ionic interactions with SPC was shown to contribute to higher mechanical properties of Gellan modified SPC (S. Chabba, G. F. Matthews and A. N. Netravali, *Green Chemistry*, 2005, 7, 576-581; and P. Lodha and A. N. Netravali, *Polymer composites*, 2005, 26, 647-659). The SPC composite resin containing 1.5 parts of glycerol, 40 parts of MFC and 0 parts gellan showed Young's modulus of 4.5 GPa and fracture stress of 85 MPa while with 40 parts of gellan, the combination showed impressive Young's modulus of 5.8 GPa and fracture stress of 122 MPa (P. Lodha and A. N. Netravali, *Polymer composites*, 2005 26, 647-659). Huang and Netravali (*Biomacromolecules*, 2006, 7, 2783-2789; *Compos Sci Technol*, 2009, 69, 1009-1015; *Journal of Macromolecular Science, Part A: Pure and Applied Chemistry*, 2008, 45, 899-906; and *Compos Sci Technol*, 2007, 67, 2005-2014) also reported the tensile properties of SPI and SPI reinforced with fillers such as micro/nano fibrillated cellulose (MFC), nanoclay, flax yarns etc. where the values of Young's modulus obtained were up to 4.3 GPa. It should be mentioned that in the present case the addition of MFC turns the resin into a nanocomposite making much stronger and stiffer resin. Never the less, the increase in mechanical properties after crosslinking is significant. The crosslinked SF resin can be easily used for making 'green' composites by reinforcing it with natural cellulose fibers. FIG. 10 shows a typical SEM image of the fracture surface of the crosslinked SF. The fracture surface is rough with a layered structure, indicating brittleness of the specimen. Similar fracture surface topography for crosslinked protein was also reported by Lodha and Netravali (P. Lodha and A. N. Netravali, *Polymer composites*, 2005, 26, 647-659) who crosslinked SPI with Phytagel®. However, as discussed earlier the specimen is only lightly crosslinked and the fracture is not caused by catastrophic failure as is common for highly crosslinked, hard and completely brittle polymers. This is also in agreement with other researchers who studied the crosslinking of soy protein (X. Huang and A. N. Netravali, *Composites Science and Technology*, 2009, 69, 1009-1025; P. Lodha and A. N. Netravali, *Polymer composites*, 2005 26, 647-659; J. T. Kim and A. N. Netravali, *Composites Part A: Applied Science and Manufacturing*, 2010, 41, 1245-1252; and M. Iman et al., *Journal of Applied Polymer Science*, 2012).

Example 2

Plant Protein-Based Crosslinked Nanofiber Membranes

Developing the green and sustainable alternative materials to replace petroleum based materials is a current need in society. Such green materials may be easily composted after their life completing the nature's carbon cycle. In the current example, novel, green, and plant protein based nanofiber membranes were fabricated without the use of any toxic solvent or crosslinking agent. Defatted soy flour which contains about 55% protein was purified using an acid-wash process to obtain material with higher protein content and successfully electrospun into nanofiber membranes with the help of polyvinyl alcohol and gluten. Oxidation of sucrose with hydrogen peroxide was carried out to synthesize oxidized sugar containing aldehyde groups. The crosslinking of protein based films and nanofiber membranes, using oxidized sugar, was confirmed by FTIR, sol-gel test and change in the color that results from the Maillard reaction. Finally, crossliking quality of protein based nanofiber membrane by oxidized sugars was found to be similar to membranes crosslinked using glyoxal. This novel green and relatively low cost method to fabricate and crosslink protein based nanofiber membranes can be useful in making inexpensive products with very high specific surface areas and highly porous structures.

Materials and Methods

Purification of SF

Figure 11:
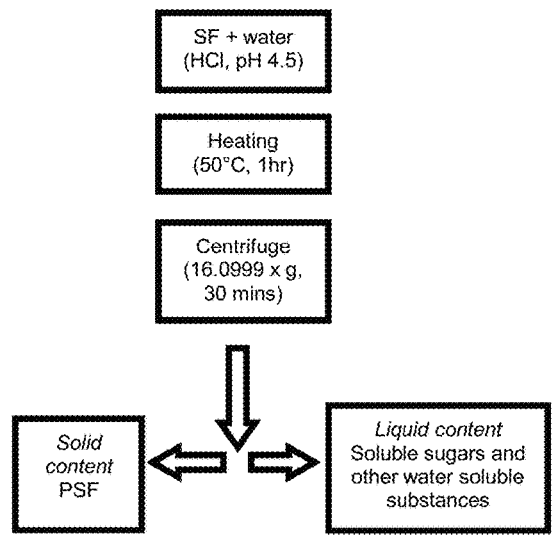
FIG. 11: Scheme for purification of soy flour to obtain PSF.

SF obtained from Archer Daniels Midland Company (Decatur, Ill., USA) was purified using an acid-wash process to obtain PSF with higher protein content. 10 g of soy flour was dissolved in 100 mL deionized (DI) water and the solution pH was lowered to 4.5 using HCl. The acidified SF solution was afterwards heated to 50° C. for 1 hr. Soy protein becomes insoluble in water at its isolectric point (pH 4.5) and the molecules precipitate, while the sugars remain soluble. As a result, sugars can be filtered out easily from the SF solution increasing its protein content. Centrifuging was found to be useful to separate most of the soluble sugars leaving a PSF residue with a high protein concentration. For this reason, the SF solution was centrifuged for 30 minutes at 16.099×g when the precipitated protein was obtained in solid form. The scheme for the SF purification process to obtain PSF is shown in FIG. 11.

Synthesis of OS by Oxidation of Sucrose 10 g of sucrose obtained from VWR was oxidized using 100 ml of 30% $H_2O_2$ at pH 2 (using HCl) (T. Ghosh-Dastidar et al., *Green Chem.*, 2013, 15, 3243-3251). The oxidation reaction was carried out for 30 min at 45° C., with occasional shaking. Finally, the solution was heated in an oven for two days at 45° C. to obtain complete oxidation.

Fabrication of Nanofiber Protein Based Membrane

Powdered PVA with molecular weight of 130,000 g·mol$^{-1}$ was purchased from Sigma Aldrich, (St. Louis, Mo.) and gluten was purchased from MGP Ingredients, (Atchison, Kans.).

Polymer solutions with different compositions of PSF, PVA and gluten were blended to obtain different protein contents in the resulting nanofiber membrane. To obtain the highest possible protein content in nanofiber membrane which contained minimum number or no polymer beads or other defects was one of the main aims of this study. PVA was initially dissolved in DI water at room temperature overnight to obtain a polymer concentration of 14% (by wt). Gluten, and PSF were individually dissolved in water and the solution pH was adjusted to 11 using NaOH while being heated at 60° C. for 30 min. This step was performed to denature the protein and open up the molecules. Solution concentrations for gluten and PSF were kept at 10 and 12% (by wt), respectively. Thereafter, the individually prepared solutions were mixed together at room temperature in different volume composition to obtain the desired blend proportions of proteins/PVA and stirred for 2 hrs. Various combinations of polymer solutions used in the study are presented in Table 3. Triton X-100 (0.5 wt %) was added to all solutions as a non-ionic surfactant to obtain uniform dispersion of the protein molecules.

TABLE 3

Polymer blends used for preparation of nanofiber membrane

| Polymer blend | Dry basis composition |
| --- | --- |
| PSF/PVA | [36/64] |
| PSF/PVA | [46/54] |
| Gluten/PVA | [46/54] |
| Gluten/PSF/PVA | [36/26/38] |
| Gluten/PSF/PVA | [30/25/45] |

Nanofiber membranes were prepared by needle electrospinning for all polymer compositions in Table 3. Electrospinning was carried out at a voltage of 25 kV, an electrode-collector distance of 15 cm and a flow rate of 0.015 ml·min$^{-1}$. Electrospun nanofibers were deposited on a polypropylene spunbonded substrate.

Crosslinking of Protein Based Film and Nanofiber Membrane

Two different crosslinking agents, glyoxal and OS, were used to obtain gluten/PSF/PVA resin with higher stability in water. Glyoxal is commercially available but a more toxic option and the laboratory synthesized OS was used as the green option. Glyoxal is known to crosslink proteins (M. A. Glomb et. al., *J. Biol. Chem.*, 1995, 270, 10017-10026) and was used as a benchmark for comparing the quality of the crosslinking gluten/PSF/PVA nanofiber membranes or films by OS.

Aqueous solution of glyoxal (40%) and 85% phosphoric acid ($H_3PO_4$), used as catalyst, were purchased from VWR International. As mentioned earlier, PVA was dissolved in DI water to obtain 14% concentration. Glyoxal with $H_3PO_4$ were added to PVA solutions in three different concentrations 2 hrs before blending with gluten/PSF polymer solution. PVA with gluten/PSF polymer solution was stirred for 2 hrs at room temperature thereafter. Dry basis composition of the final polymer blend was [30/25/45 gluten/PSF/PVA] and the concentration of glyoxal was 5, 10 and 15% (by wt). The surfactant, Triton X-100, was added in concentration of 0.5% (by wt) to all solution mixtures, as the final step.

As stated earlier, OS was tested as the green crosslinking agent. OS was added into gluten/PSF solutions in different concentrations and stirred for 1 hr at 70° C. PVA was added into gluten/PSF polymer solution afterwards and stirred for 2 hrs at room temperature. The final polymer blend on dry wt basis was [30/25/45 gluten/PSF/PVA] and concentration of OS was varied at 5, 10 and 15%. As in the case of glyoxal, Triton X-100 as surfactant was added in concentration of 0.5% into all solution mixtures.

Gluten/PSF/PVA films with crosslinking agents were prepared by casting polymer solution into round petri dishes (50 mm dia) which were kept in an air circulating oven at 45° C. for overnight drying. The crosslinking reaction was achieved by heating the resulting films in the oven at 100° C. for 30 mins.

Nanofiber membranes of gluten/PSF/PVA with both crosslinking agents, glyoxal and OS, were prepared by electrospinning process of polymer solutions. The crosslinking reaction was completed to the maximum extent possible by heating the nanofiber membranes in an air circulating oven at 100° C. for 30 mins, the same process used in the case of films.

Characterization of Protein Based Nanofiber Membranes

The surface morphologies of nanofiber membranes were characterized using a scanning electron microscope (SEM, LEO 1550 FE-SEM, Zeiss) at an accelerating voltage of 15 kV. The specimens were adhered by double-sided electrically conductive carbon tape and then coated with a thin gold layer before observing in SEM.

Both OS and crosslinked nanofiber membranes were characterized using an FTIR spectrophotometer (Nicolet Magna-IR 560, Thermo Scientific). ATR-FTIR spectra were taken in the range of 4000-550 cm$^{-1}$ wavenumbers using a split peak accessory. Each scan was an average of 64 scans obtained at a resolution of 4 cm$^{-1}$ wavenumber. Reproducibility was confirmed for each type of specimen by repeating the experiment three times. The spectra of sucrose and OS as well as nanofiber membranes made of gluten/PSF/PVA with 0, 5 and 10% OS before and after crosslinking were compared.

Characterization of Crosslinked Protein Based Films by Sol-Gel Test

The gel content, g (%) of films prepared from gluten/PSF/PVA with 5, 10 and 15% (by wt) of glyoxal and OS was calculated as previously described (O. Wichterle et al., *Nature*, 1960, 185, 117-118; N. A. Peppas et al., *Annu. Rev. Blamed. Eng.*, 2000, 02, 9-29; and A. S. Hoffman, *Adv. Drug Delivery Rev.*, 2002, 43, 3-12), according to Eq.s 1 and 2, where $w_d$ is the weight of the dry film before extraction and $w_0$ is the weight of the film after extraction. Films were fully dried at 60° C. for 24 hrs prior to conducting the sol-gel tests. The extractions were done in Erlenmeyer flasks with DI water which were placed on a shaker table (MAXQ 4450, Thermo Scientific) at 175 rpm for 3 hrs at the temperature 60° C. The solid contents after extraction were filtered using a Whatman filter paper (no. 4, qualitative) to obtain final residues and dried to constant weight (60° C. for 24 hours).

Stability of the films in water was tested under two conditions: (i) 6 hrs at 80° C. and (ii) 1 month at room temperature (21° C.).

$$s(\%) = \left(\frac{w_d - w_0}{w_d}\right) \times 100 \qquad (1)$$

$$g(\%) = 100 - s(\%) \qquad (2)$$

Results and Discussion

Purification of SF

The protein contents in the SF, gluten and laboratory prepared PSF were measured by elemental analysis. The average protein content values obtained from 3 separate tests are presented in Table 4.

TABLE 4

Protein content in SPC, SF, PSF and gluten analyzed by elemental analysis technique

| Type of protein source | Protein content [%] |
|---|---|
| SPC | 64.4 |
| SF | 52.2 |
| PSF | 66.1 |
| Gluten | 77.7 |

It was found out that purification of SF carried out in the laboratory was successful and the protein content in PSF reached 66.1%, up from 52% for SF and was comparable to the protein content of 64.4% in commercial SPC. The repeatability of the purification process was confirmed by measuring the protein content on three independent purification tests. The standard deviation for the protein content for PSF was 1% of the average protein content value. Based on these results it was concluded that it is possible to prepare PSF in the laboratory from SF, comparable to commercially available SPC, using the acid wash process. Commercial gluten was used without modification, since it contained high protein content over 77%. Material lost, mostly a mixture of sugars, during production of PSF was analyzed and was found to contain up to 17% protein. The lost material during the purification of SF amounted to about 44%.

Characterization of OS

Aldehydes (—CHO) are reactive varieties of the more general functional group, carbonyl (C=O). The polarity of this bond (especially in the context of aldehydes) makes the carbon atom electrophilic and reactive to nucleophiles such as primary amines. Aldehydes can be created wherever oxidizable sugar groups exist (S. S. Wong et al., *National Institutes of Health*; CRC Press, USA, 1991; and T. Ghosh-Dastidar et al., *Green Chem.*, 2013, 15, 3243-3251).

Figure 12:
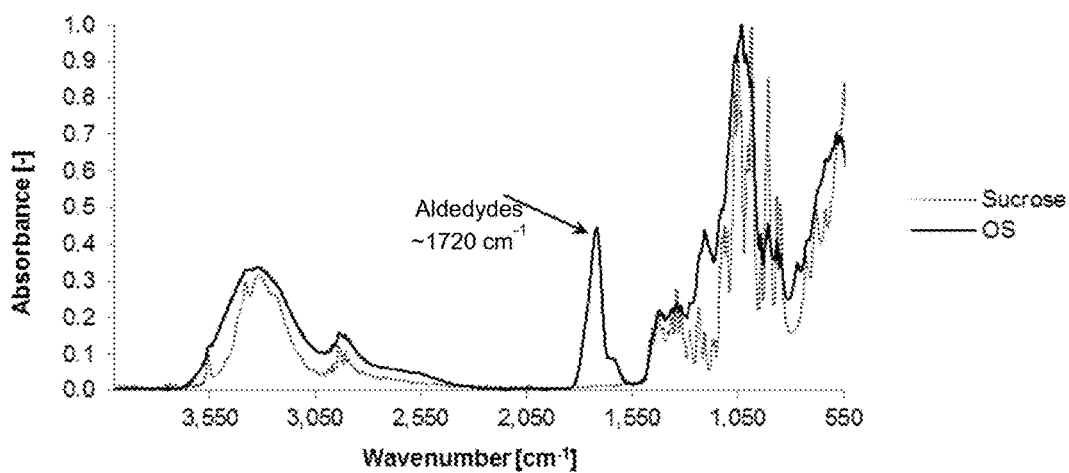
FIG. 12: FTIR spectra of prepared OS.

Oxidation of sucrose was realized by $H_2O_2$ to generate dialdehyde molecules, which were afterwards used as a crosslinking agent for gluten/PSF/PVA. ATR-FTIR spectra of sucrose before and after oxidation are shown in FIG. 12. The FUR analysis clearly showed the absorption peak at 1720 $cm^{-1}$ for OS which confirms the aldehyde functional group in the sugar after oxidation. However, it is possible that OS also contains carboxyl (—COOH) groups which also results in absorption at 1720-1725 $cm^{-1}$ (T. Ghosh-Dastidar et al., *Green Chem.*, 2013, 15, 3243-3251). However, the carboxyl group can also react with the amine groups to form amide group or with hydroxyl group to form ester group. The aqueous process that used benign $H_2O_2$ as green oxidizing reagent for converting sucrose into a cross-linking agent can be considered as a green process as noted by earlier researchers (Id.).

Electrospinning of Protein Based Polymer Solutions

The electrospinning study was carried out to investigate the spinnability of various solutions that contained different amounts of protein. As mentioned earlier, one of the main goals of this study was to obtain the highest possible plant based protein content in the nanofiber membranes with least amount of beads and/or other defects. Pure PSF polymer solution heated to 60° C. for 30 min and alkali-treated (pH 11) could not be spun into nanofibers. The continuous and uniform fiber formation of pure PSF via electrospinning was found to be difficult, possibly because of the complex network structures of soy protein in the aqueous solution (Wolf et al., *J. Agric. Food Chem.*, 1992, 40, 1809-1816; and J. M. S. Renkema, *Formation, Structure and Rheological Properties of Soy Protein Gels*. PhD Thesis, Wageningen University:Netherland, April 2011). However, when PVA was added, as 'helper polymer', to form PSF/PVA, or gluten/PSF/PVA solutions, they could be readily electrospun into nanofibers. FIG. 13 shows SEM images of nanofiber membranes formed by PSF/PVA [46/54], [36/64], gluten/PVA [46/54] and gluten/PSF/PVA [36/26/38], [30/25/45] compositions.

Figures 13A, 13B, 13C, 13D, 13E:
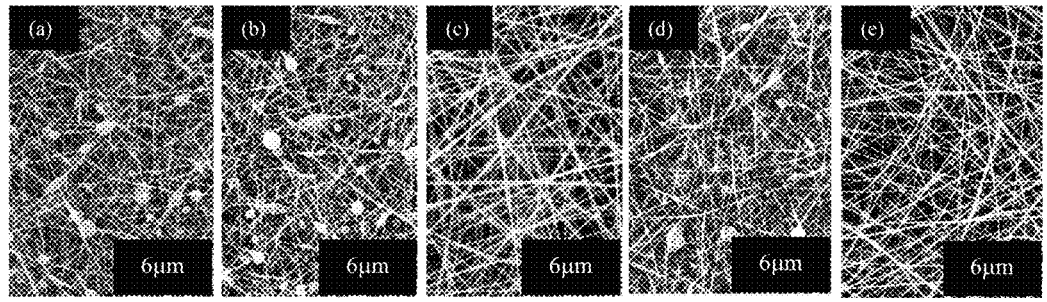
FIGS. 13A-13E: Nanofiber membranes consisting of: PSF/PVA [46/54] (FIG. 13A), gluten/PVA [46/54] (FIG. 13B), PSF/PVA [36/64] (FIG. 13C), gluten/PSF/PVA [36/26/38] (FIG. 13D), and gluten/PSF/PVA [30/25/45] (FIG. 13D).

As can be seen from FIG. 13, electrospinning of PSF/PVA [46/54] or gluten/PVA [46/54] solutions led to nanofiber structure that contained a few polymer beads. The best nanofiber structures without polymer beads, however, were formed in the case of PSF/PVA [36/64] blend. To reach the maximum protein content in the nanofiber membrane, gluten/PSF/PVA composition was tested. Nanofiber structure was obtained for gluten/PSF/PVA composition with dry basis close to [30/25/45]. In this case, a decrease in PVA content in the polymer blend gluten/PSF/PVA to [36/26/38] led to fiber structure with defects. It was noted, from all the experiments that increase of the PVA content in the polymer composition leads to more uniform fibrous structure. This effect can be attributed partially to the linear nature of PVA as well as increase in viscosity that results in enhanced polymer chain entanglement which reduces the surface tension effect and prevents bead formation (D. Cho et al., *Macromol. Mater. Eng.*, 2010, 295, 763-773). These observations indicate that help from PVA is required to produce protein based nanofibers, perhaps because of the helical nature of the protein. Nevertheless, protein content of up to 55% could be electrospun into good nanofibers as shown in FIG. 13E.

Electrospinnable blend gluten/PSF/PVA [30/25/45] was chosen for the crosslinking study because of the lowest content of PVA and the highest content of protein in the nanofiber membrane. Two different crosslinking agents: (i) glyoxal and (ii) OS were used to crosslink the protein blend.

Figures 14A, 14B, 14C:
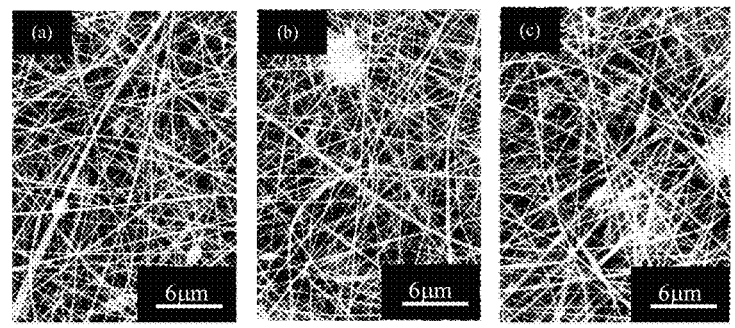
FIGS. 14A-14C: Nanofiber membranes gluten/PSF/PVA [30/25/45] with glyoxal: 5 wt % (FIG. 14A), 10 wt % (FIG. 14B), and 15 wt % (FIG. 14C).

Electrospinning of gluten/PSF/PVA composition with 5, 10 and 15% of glyoxal (by wt) led to very similar fiber structure and contained only few polymer beads as shown in FIG. 14. The beads were possibly due to partially cross-linked polymer.

Figures 15A, 15B, 15C:
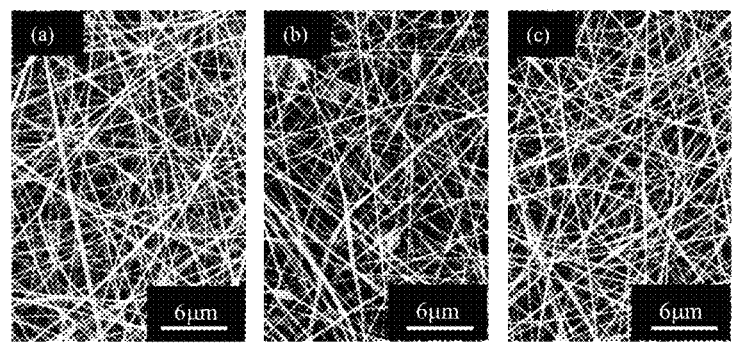
FIGS. 15A-15C: Nanofiber membranes gluten/PSF/PVA [30/25/45] with OS: 5 wt % (FIG. 15A), 10 wt % (FIG. 15B), and 15 wt % (FIG. 15A).

Electrospinning of gluten/PSF/PVA solution with 5, 10 and 15% of OS however, led to the most uniform nanofiber structure with no polymer beads. These fiber structures are shown in FIG. 15. It is clear from these images that the fibers are uniformly, cylindrical shape and within a narrow range of fiber diameters. This is perhaps because of the lower crosslink density with OS compared to glyoxal.

Characterization of Crosslinked Protein Based Nanofiber Membranes and Films

FIG. 16 shows the ATR-FTIR spectra of the gluten/PSF/PVA nanofiber membranes without crosslinking reagent and after crosslinking reaction with 5 and 10% of OS. All spectra were normalized based on bands observed at 550 $cm^{-1}$ wavenumber. Also atmospheric correction was used for all spectra.

The ATR-FTIR analysis of the nanofiber membranes was based on the identification of absorption bands related to the functional groups present in gluten, PSF, PVA and OS. A broad band at 3050-3550 $cm^{-1}$ wavenumber is a result of the hydroxyl (—OH) stretching vibration resulting from the presence of strong hydrogen bonds of intra-molecular and inter-molecular hydrogen bonds, in PVA as well as amino (—NH) groups (J. M. Gohil et al., *J. Polym. Res.*, 2006, 13, 161-169; and H. S. Mansur et al., *Mater. Sci. Eng. C*, 2008, 28, 539-548). The absorption band observed between 2820 and 3000 $cm^{-1}$ wavenumber is due to the stretching of aliphatic C—H bond (H. S. Mansur et al., *Mater. Sci. Eng. C*, 2008, 28, 539-548). The absorption bands in the range of 1630-1680 $cm^{-1}$ and 1533-1559 $cm^{-1}$ correspond to amide I band (associated with the C═O stretching vibration and N—H bending) at 1630 cm' and amide II band (N—H bending and C—N stretching) at 1530 $cm^{-1}$, respectively, and confirm earlier observations by others (K. K. Chittur, *Biomaterials*, 2006, 19, 357-369; and C. F. Lu et al., *J. Colloid. Interf. Sci.*, 1994, 168, 152-161).

As can be seen in the spectra shown in FIG. 16, absorptions in the range of 1630 and 1530 $cm^{-1}$ shifted down after crosslinking the gluten/PSF/PVA nanofiber membranes. The strong amide band present in soy protein disappeared and a new absorption band at 1715 $cm^{-1}$ appeared after crosslinking. This spectral change indicates reduction in the C═O (amide I band) and N—H (amide II band) in the specimens as a result of crosslinking reaction with the aldehyde groups in the OS. This can be explained by the following hypothesis. The aldehyde groups present in the crosslinking agent OS react with primary amino groups of the soy protein, primarily lysine and arginine, and possibly with —OH groups appeared in PVA (K. Qiu et al., *Polym. Composite*, 2013, 34, 799-809; and K. Qiu et al., *J. Mater. Sci.*, 2012, 47, 6066-6075). These reactions where amines and carbonyl compounds, especially the aldehydes in OS, react together and are responsible for the crosslinking and are referred to as Maillard reactions. The Maillard reaction is strongly dependent on reaction conditions such as duration and temperature of reaction, pH and type of sugar present (M. A. Glomb et. al., *J. Biol. Chem.*, 1995, 270, 10017-10026). For that reason heating and addition of NaOH to gluten/PSF/PVA solution were carried out to stabilize the conjugation as well as to denature the protein, i.e., open up the molecules. The Maillard reaction is also responsible for changes in the color and is described later. The shift in absorption band observed at 1050-1150 $cm^{-1}$ wavenumber could indicate possible crosslinking reaction and presence of sulfoxide bonds. Disulfide bonds formed through the cystiene amino acids, may be also present, but were not observed due to the low sensitivity of the IR technique. Similar difficulties have been expressed by others as well (R. Nakamura et al., *Fire Mater.*, 2012, 37, 75-90; and X. Huang et al., *J. Macromol. Sci., Part A: Pure and Applied Chemistry*, 2008, 45, 899-906). However, the crosslinking could be easily confirmed using other characterization techniques including change in color and sol-gel analysis.

As mentioned above, nucleophilic varieties of primary amines (—$NH_2$) are the main class of compounds that react with aldehydes. Since primary amines are abundant in proteins, it is important to remember that aldehydes represent amine-reactive crosslinker chemistry just as much as primary amines constitute aldehyde-reactive crosslinker chemistry (S. S. Wong et al., *National Institutes of Health*; CRC Press, USA, 1991).

The Maillard reaction known synonymously as the "non-enzymic browning reaction" has long been recognized and quantified as the source of color in processed foods such as bread, and of colors associated with food deterioration (P. R. George, *Food Rev. Int.*, 1997, 13, 1-28). The coloration of the gluten/PSF/PVA films intensified from pale yellow to brown as shown in FIG. 17, depending on the concentration of OS in gluten/PSF/PVA films. The change in color also indicates the extent of Maillard reaction.

Sol-Gel Analysis of Crosslinked Protein Based Films

Sol-gel analysis was performed for gluten/PSF/PVA films that were crosslinked by different crosslinking agents: 5, 10 and 15% of glyoxal and OS. FIG. 18 presents the sol-gel test results for all the films. The results indicate that the gel (crosslinked) percentage g (%) of the crosslinked gluten/PSF/PVA by glyoxal was 70-78% depending on the concentration of glyoxal. As can be expected, the gel percentage increased with higher glyoxal content. Since the main reaction is between the amine groups in protein and aldehyde groups in glyoxal and that the hydroxyl groups in PVA is minimal, the g % of 70-78% is considered reasonable. As compared to glyoxal, approximately 54-61% of the crosslinked gluten/PSF/PVA was found out for films crosslinked using OS. Nevertheless, the results of this test (FIG. 18) demonstrate that the OS did work as a crosslinker but the level of crosslinking was lower in comparison to glyoxal. This is mainly because of higher number of aldehyde groups present in glyoxal. In the case of OS, as mentioned earlier, carboxyl groups are also created along with the aldehyde groups (T. Ghosh-Dastidar et al., *Green Chem.*, 2013, 15, 3243-3251). All tested films were swollen after being soaked in water although they remained unbroken and intact.

Films prepared from gluten/PSF/PVA polymer composition without any crosslinking agent disintegrated in water after 3 hrs when kept at the elevated temperature of 60° C. None of the films prepared from gluten/PSF/PVA composition with glyoxal dissolved after any of the testing conditions of 3 hrs at 60° C., 6 hrs at 80° C. or 1 month at the room temperature. Films prepared from gluten/PSF/PVA composition with 5 wt % of OS did not dissolve in water after 3 hrs at the temperature 60° C. as well. However, after 6 hrs at 80° C. they seem to disintegrate. Films prepared from gluten/PSF/PVA composition with 10 and 15 wt % of OS did not dissolve when kept in water for 1 month at the room temperature. Structures of films immersed in water after 1 month at the room temperature are shown in FIG. 19.

Water resistance of crosslinked and non-crosslinked nanofiber membranes was tested last. After crosslinking, the nanofiber membrane with 15% of OS was dried and immersed into DI water for 6 hrs and 1 day at the room temperature. Non-crosslinked nanofiber membrane dissolved immediately in DI water. Typical SEM images presented in FIG. 20 show changes in the nanofibers morphology after crosslinking and water treatment for 6 hrs and 1 day. Nanofibers were clearly seen to have swollen after water treatment for 6 hrs compared to unsoaked nanofibers shown in FIGS. 13, 14, and 15. However, the nanofiber membrane retained the fiber structure after 1 day water treatment though the pores almost disappeared due to swelling.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

All references cited herein are incorporated herein by reference in their entirety and for all purposes to the same extent as if each individual publication, patent or patent application was specifically and individually indicated to be incorporated by reference in its entirety for all purposes.

Citation of a reference herein shall not be construed as an admission that such reference is prior art to the present invention. All references cited herein are hereby incorporated by reference in their entirety.

What is claimed is:

1. A method of making a crosslinked thermoset resin from soy flour, said method comprising:
    separating a plant-derived flour mixture into a protein fraction comprising proteins and a carbohydrate fraction comprising carbohydrates, thereby causing said protein fraction and said carbohydrate fraction to become isolated from one another, wherein said plant-derived flour mixture is soy flour;
    subjecting said carbohydrate fraction to an oxidizing agent to yield oxidized carbohydrates comprising aldehyde functional groups or both aldehyde functional groups and carboxyl functional groups, thereby causing said oxidized carbohydrates to be effective as a crosslinking agent for said protein fraction; and
    reacting said oxidized carbohydrates produced from the subjecting step directly with said protein fraction produced from the separating step under conditions effective to cause said oxidized carbohydrates to act as a crosslinking agent for said protein fraction so as to crosslink the proteins, thereby yielding a crosslinked thermoset resin.

2. The method according to claim 1, wherein the step of reacting the oxidized carbohydrates directly with the protein fraction comprises:
    denaturing the proteins of the protein fraction to expose reactive functional groups on the denatured proteins; and
    directly contacting the oxidized carbohydrates with the functional groups of the denatured proteins to crosslink the proteins.

3. The method according to claim 1, wherein said carbohydrates comprise soluble carbohydrates comprising a sugar selected from the group consisting of glucose, fructose, sucrose, raffinose, maltose, galactose, stachyose, and mixtures thereof.

4. The method according to claim 1 further comprising:
    electrospinning a composition comprising the crosslinked thermoset resin into a nanofiber, a nanofiber membrane, or a composite.

5. The method according to claim 1, wherein the oxidizing agent is selected from the group consisting of $CrO_3$, $KMnO_4$, $HNO_3$, and $HIO_6$.

6. The method according to claim 1, wherein the oxidizing agent is a benign or non-toxic oxidizing agent.

7. The method according to claim 6, wherein the benign or non-toxic oxidizing agent is hydrogen peroxide.

8. The method according to claim 7, wherein the hydrogen peroxide is acidified.

9. The method according to claim 1, wherein the step of separating the plant-derived flour mixture into the protein fraction and the carbohydrate fraction comprises performing either a water-based separation procedure or a solvent-based separation procedure.

10. The method according to claim 9, wherein the water-based separation procedure comprises an isoelectric filtration process whereby the proteins are rendered insoluble at their isoelectric point in water while the carbohydrates remain soluble in water.

11. A method of making a crosslinked thermoset resin from a grain having carbohydrates in the form of sugars rather than starch, said method comprising:
    separating a plant-derived flour mixture into a protein fraction comprising proteins and a carbohydrate fraction comprising carbohydrates, thereby causing said protein fraction and said carbohydrate fraction to become isolated from one another, wherein said plant-derived flour mixture is a flour from a grain having carbohydrates in the form of sugars rather than starch, and wherein said grain is not corn;
    subjecting said carbohydrate fraction to an oxidizing agent to yield oxidized carbohydrates comprising aldehyde functional groups or both aldehyde functional groups and carboxyl functional groups, thereby causing said oxidized carbohydrates to be effective as a crosslinking agent for said protein fraction; and
    reacting said oxidized carbohydrates produced from the subjecting step directly with said protein fraction produced from the separating step under conditions effective to cause said oxidized carbohydrates to act as a crosslinking agent for said protein fraction so as to crosslink the proteins, thereby yielding a crosslinked thermoset resin.

12. The method according to claim 11, wherein the step of reacting the oxidized carbohydrates directly with the protein fraction comprises:
    denaturing the proteins of the protein fraction to expose reactive functional groups on the denatured proteins; and
    directly contacting the oxidized carbohydrates with the functional groups of the denatured proteins to crosslink the proteins.

13. The method according to claim 11, wherein said carbohydrates comprise soluble carbohydrates comprising a sugar selected from the group consisting of glucose, fructose, sucrose, raffinose, maltose, galactose, stachyose, and mixtures thereof.

14. The method according to claim 11 further comprising:
    electrospinning a composition comprising the crosslinked thermoset resin into a nanofiber, a nanofiber membrane, or a composite.

15. The method according to claim 11, wherein the oxidizing agent is selected from the group consisting of $CrO_3$, $KMnO_4$, $HNO_3$, and $HIO_6$.

16. The method according to claim 11, wherein the oxidizing agent is a benign or non-toxic oxidizing agent.

17. The method according to claim 16, wherein the benign or non-toxic oxidizing agent is hydrogen peroxide.

18. The method according to claim 17, wherein the hydrogen peroxide is acidified.

19. The method according to claim 11, wherein the step of separating the plant-derived flour mixture into the protein fraction and the carbohydrate fraction comprises performing either a water-based separation procedure or a solvent-based separation procedure.

20. The method according to claim 19, wherein the water-based separation procedure comprises an isoelectric filtration process whereby the proteins are rendered insoluble at their isoelectric point in water while the carbohydrates remain soluble in water.

* * * * *